(12) United States Patent
Niazi et al.

(10) Patent No.: US 10,076,529 B1
(45) Date of Patent: *Sep. 18, 2018

(54) SMALL MOLECULE INHIBITORS OF INFLUENZA A RNA-DEPENDENT RNA POLYMERASE

(71) Applicant: Nant Holdings IP, LLC, Culver City, CA (US)

(72) Inventors: Kayvan Niazi, Encino, CA (US); Shahrooz Rabizadeh, Los Angeles, CA (US); Anne-Laure Le Ny, South Pasadena, CA (US); Oleksandr Buzko, Los Angeles, CA (US); Justin Golovato, Los Angeles, CA (US); Patrick Soon-Shiong, Los Angeles, CA (US)

(73) Assignee: NANT HOLDINGS IP, LLC, Culver City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/068,379

(22) Filed: Mar. 11, 2016

Related U.S. Application Data

(63) Continuation of application No. 14/170,353, filed on Jan. 31, 2014, now Pat. No. 9,315,464.

(60) Provisional application No. 61/759,290, filed on Jan. 31, 2013.

(51) Int. Cl.

| | |
|---|---|
| *A61K 31/635* | (2006.01) |
| *A61K 31/426* | (2006.01) |
| *A61K 31/454* | (2006.01) |
| *A61K 31/444* | (2006.01) |
| *A61K 31/496* | (2006.01) |
| *A61K 31/4709* | (2006.01) |
| *A61K 31/4409* | (2006.01) |
| *A61K 31/47* | (2006.01) |
| *A61K 31/5377* | (2006.01) |
| *A61K 31/501* | (2006.01) |
| *A61K 31/55* | (2006.01) |
| *G06F 19/12* | (2011.01) |
| *A61K 31/4545* | (2006.01) |

(52) U.S. Cl.
CPC ......... *A61K 31/635* (2013.01); *A61K 31/426* (2013.01); *A61K 31/444* (2013.01); *A61K 31/4409* (2013.01); *A61K 31/454* (2013.01); *A61K 31/4545* (2013.01); *A61K 31/47* (2013.01); *A61K 31/4709* (2013.01); *A61K 31/496* (2013.01); *A61K 31/501* (2013.01); *A61K 31/5377* (2013.01); *A61K 31/55* (2013.01); *G06F 19/12* (2013.01)

(58) Field of Classification Search
CPC ............. A61K 31/635; A61K 31/4709; A61K 31/454; A61K 31/444; A61K 31/4545; A61K 31/496; A61K 31/426; A61K 31/4409; A61K 31/47; A61K 31/5377; A61K 31/501; A61K 31/55; G06F 19/12

See application file for complete search history.

(56) References Cited

U.S. PATENT DOCUMENTS

| | | |
|---|---|---|
| 6,258,585 B1 | 7/2001 | Draper |
| 7,276,356 B1 | 10/2007 | Palese et al. |
| 8,008,269 B2 | 8/2011 | Vaillant et al. |
| 9,315,464 B1 * | 4/2016 | Niazi ............... C07D 215/52 |
| 2006/0025415 A1 * | 2/2006 | Gonzalez, III ....... C04B 35/632 |
| | | 514/235.5 |
| 2009/0163545 A1 * | 6/2009 | Goldfarb ............. A61K 31/122 |
| | | 514/312 |

FOREIGN PATENT DOCUMENTS

| | | | |
|---|---|---|---|
| CN | 101108186 A | * | 1/2008 |
| DE | 695 24 618 T2 | | 8/2002 |
| WO | 1993-23569 A1 | | 11/1993 |
| WO | WO 2003/037887 A1 | * | 5/2003 |
| WO | WO 2004/031158 A1 | * | 4/2004 |
| WO | WO 2010/039538 A1 | * | 8/2010 |
| WO | WO 2014/055548 A1 | * | 4/2014 |

OTHER PUBLICATIONS

CN 101108186 A English machine translation ProQuest Dialog Mar. 23, 2017 p. 1-18.*
WO 2004/031158 A1 English machine translation ProQuest Dialog Mar. 24, 2017 p. 1-93.*
Engel, D., National Center for Biotechnology Information. PubChem Bioassay Database; "qHTS Assay for Inhibitors of Influenza NS1 Protein Function" (2010), deposit date Feb. 1, 2010; accessed date Jan. 13, 2015; http://pubchem.ncbi.nlm.nih.gov/assay/assay.cgi?aid= 2326; excerpt provided, p. 1-16.*
Goldfarb, D.S., National Center for Biotechnology Information. PubChem Bioassay Database; "Screen for Chemicals that Extend Yeast Lifespan" (2007), deposit date Jul. 12, 2011; accessed date Jan. 13, 2015; http://pubchem.ncbi.nlm.nih.gov/assay/assay.cgi?aid= 775; excerpt provided, p. 1-3.*
McKim, A.S., "Dimethyl Sulfoxide USP, PhEur in Approved Pharmaceutical Products and Medical Devices." (2008), Pharmaceutical Technology, May 2008, p. 1-6.*
Sirimulla, S., "Identification of novel nitrosative stress inhibitors through virtual screening and experimental evaluation." Molecular informatics 31.2 (2012): 167-172.*

(Continued)

*Primary Examiner* — John M Mauro
(74) *Attorney, Agent, or Firm* — Lucas & Mercanti LLP

(57) ABSTRACT

Compositions, compounds, and methods with significant antiviral effect against RNA viruses and especially orthomyxoviruses are contemplated, and target the viral promoter that is formed by the 5' and 3'-UTR sequences of the viral genome.

1 Claim, 9 Drawing Sheets

(56) References Cited

OTHER PUBLICATIONS

Li, J., "Discovering novel chemical inhibitors of human cyclophilin A: virtual screening, synthesis, and bioassay." Bioorganic & medicinal chemistry 14.7 (2006): 2209-2224.*
Chen, S., "Structure-based identification of small molecule compounds targeting cell cyclophilin A with anti-HIV-1 activity." European journal of pharmacology 565.1 (2007): 54-59.*
Basse, N., "Novel organic proteasome inhibitors identified by virtual and in vitro screening." Journal of medicinal chemistry 53.1 (2009): 509-513.*
Noble, E., et al., "Biophysical Analysis of Influenza A Virus RNA Promoter at Physiological Temperatures", J. Biol. Chem. 2011, 286: 22965-22970.
Iguchi, A., et al., "RNA Binding Properties of Novel Gene Slicing Pyrrole-Imidazole Polyamides," Biol. Pharm. Bull. 36(7) 1152-1158 (2013); pp. 1152-1158.
Cheong, H., et al., "Structure of influenza virus panhandle RNA studied by NMR spectroscopy and molecular modeling," Nucleic Acids Research, 1999, vol. 27, No. 5, pp. 1392-1397.
Bae, S., et al., "Structural features of an influenza virus promoter and their implications for viral RNA synthesis," PNAS Sep. 11, 2001, vol. 98, No. 19, pp. 10602-10607.
Kinnamon, K.E., "Trypanosoma cruzi:A Novel Chemical Class (Nitrobenzofurans) Active against Infections of Mice (*Mus musculus*)." Experimental parasitology 89.2 (1998): 251-256.
McKim, A.S., "Dimethyl Sulfoxide USP, PhEur in Approved Pharmaceutical Products and Medical Devices" (2008), Pharmaceutical Technology, May 2008, p. 1-6.
Thorwald, R.F., List of RNAs; http://en.wikipedia.org/wiki/List%20of%20RNAs?oldid=626333112; References therein dated 1997-2009.

\* cited by examiner

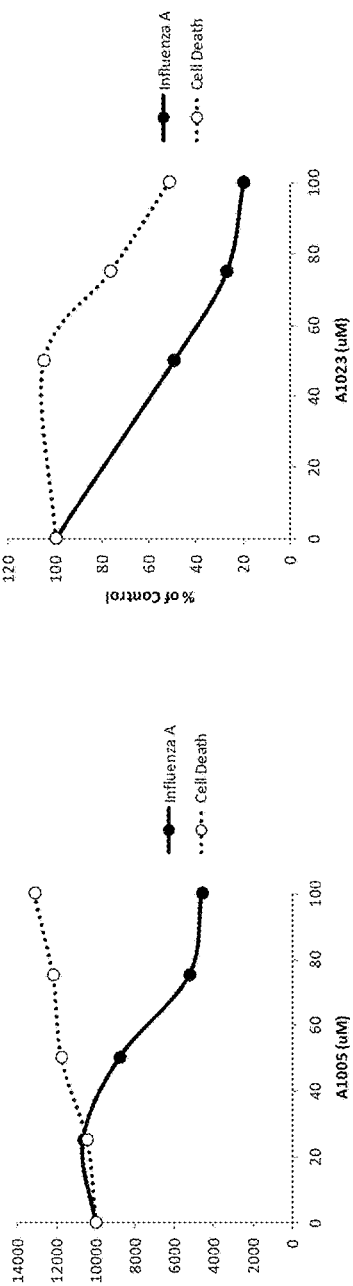
Figure 5D
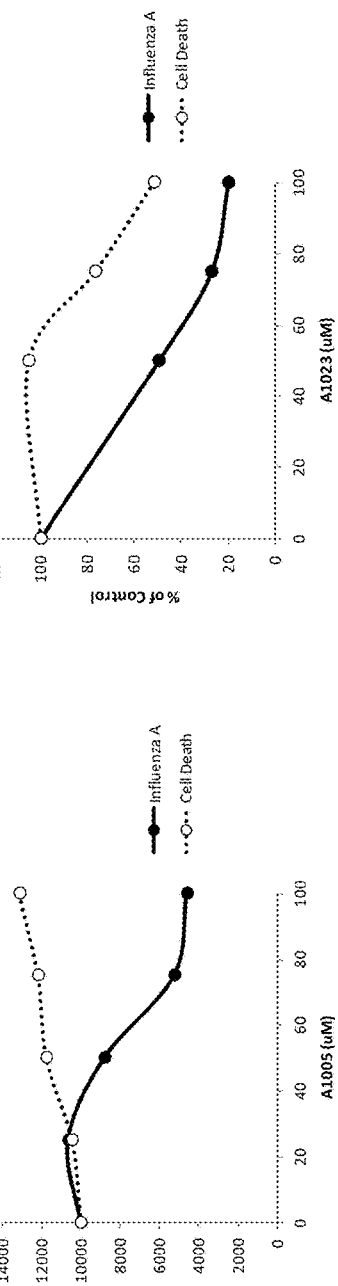
Figure 5E
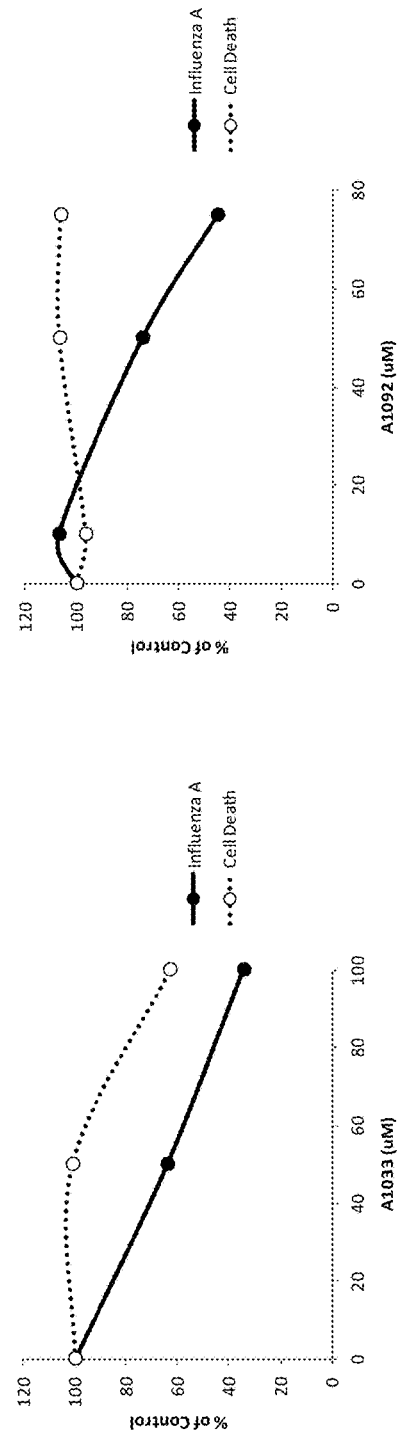
Figure 5F
Figure 5G

SMALL MOLECULE INHIBITORS OF INFLUENZA A RNA-DEPENDENT RNA POLYMERASE

This application is a continuation of U.S. application Ser. No. 14/170,353, filed Jan. 31, 2014, now U.S. Pat. No. 9,315,454, which claims priority to U.S. Provisional Application Ser. No. 61/759,290, which was filed Jan. 31, 2013, all of which are incorporated by reference herein.

FIELD OF THE INVENTION

The field of the invention is antiviral composition and methods, especially as they relate to RNA polymerase inhibitors for orthomyxoviridae, and especially for influenza viruses.

BACKGROUND OF THE INVENTION

Influenza A virus is a member of the orthomyxoviridae virus family of (−)-sense RNA viruses. The Influenza A viral genome is composed of 8 segments or chromosomes which encode 11 proteins. During infection, these (−)-stranded RNAs are converted to both (+) strand messenger RNAs and a set of full length complementary genomic RNAs (or cRNAs) which serve as templates for genomic replication by a virus-encoded RNA-dependent RNA polymerase. Viral proteins expressed from the (+) strand messenger RNAs go about the task of establishing infection and facilitating viral replication, a process which ends in the amplification, assembly, and logarithmic release of virus particles containing the initial 8 (−) strand chromosomes.

The processes associated with the transcription and replication of the influenza A genome have been under investigation for decades. All eight chromosomes of every influenza A strain (including H1N1 seasonal, H1N1 "swine", H3N2, and H5N1 "avian") contain identical 5' and nearly identical 3' untranslated regions (UTRs) flanking the protein-coding portion of the sequence which otherwise encode distinct proteins and strain-specific variants. Experimental results demonstrate that the UTRs are recognized by the viral RNA-dependent RNA polymerase (vPol) as a promoter element and highlight the importance of the UTR sequences in viral gene expression and replication. Hence, the viral polymerase and its cognate ligand control the viral life cycle and are critical targets for therapeutic intervention.

Due to the partial complementarity of the UTR sequences to each other, different models for the UTR structure recognized by vPol have been proposed, including the panhandle, RNA fork, and corkscrew conformations. Although the structure formed by the UTRs is probably dynamic, the model most likely to represent the actual structure of the UTRs and hence the promoter element for vPol-driven gene expression is the corkscrew model. The adoption of this highly unusual tetrahelical (also referred to as "corkscrew"- or "panhandle"-like) structure by the UTRs is supported by at least two different lines of evidence provided by genetic and solution NMR studies. For the former, genetic point mutants spanning the entire length of the two UTRs were created and assessed in their promoter activity and the resulting gene expression data were consistent with the corkscrew conformation model. Further studies using NMR spectroscopy solved the solution structure of a synthetic RNA possessing correctly oriented UTR sequences and again determined a corkscrew-like structure. Biochemical and genetic assays were also able to delineate the critical promoter sequences recognized by vPol as residing between nucleotides 9-12 of the UTR with the "bulge" structure in the vicinity of A11 as a central player in recognition and polyadenylation.

Further studies have provided insights to the functionality of the panhandle structure (see e.g., JBC (2011) 286, No. 26, pp. 22965-22970; NAR (1999), 27, No. 5, pp. 1392-1397). However, these insights have failed to provide a rational design approach to postulate and identify an inhibitor that would bind to the panhandle structure and thereby reduce or stop viral propagation. Only recently (see Biol. Pharm. Bull. (2013) 36(7) 1152-1158), certain pyrrole-imidazole polyamides were described as being able to bind to DNA and RNA double stranded structures. Unfortunately, the pyrrole-imidazole (PI) polyamides used showed only moderate affinity to the Influenza A panhandle structure in vitro and were not tested in vivo for any antiviral activity. All publications identified herein are incorporated by reference to the same extent as if each individual publication or patent application were specifically and individually indicated to be incorporated by reference. Where a definition or use of a term in an incorporated reference is inconsistent or contrary to the definition of that term provided herein, the definition of that term provided herein applies and the definition of that term in the reference does not apply.

More recently, high throughput screening has identified several compounds with significant antiviral activity against an apparently conserved viral target that is located within the viral replication and/or gene expression machinery, most likely the viral RNA-dependent RNA polymerase as described in U.S. Pat. No. 8,633,198. While these compounds have exhibited promising in vitro and in vivo activity, several drawbacks still remain. Among other things, where such compounds bind to a viral protein, resistance is likely to develop unless these compounds target an essential and highly conserved structure in the polypeptide.

Thus, despite the relatively detailed knowledge of the promoter structure and life cycle of influenza viruses, drug development for inhibitors of viral replication has not yielded the desired therapeutically effective compounds that target the viral UTR sequences that appear to be essential for viral replication and protein expression. Moreover, there is also a lack of rational drug design approaches for viral inhibitors that is independent of first-pass in vitro high throughput screening. Therefore, there is still a need to provide improved antiviral compositions and methods, and especially those that are specific for seasonal, pandemic, and emerging influenza viruses.

SUMMARY OF THE INVENTION

The present inventive subject matter is drawn to antiviral compositions and methods targeting viral UTR sequences, and especially compositions and methods that target the 5'/3'-UTR panhandle RNA sequences of influenza viruses of seasonal, pandemic, and emerging influenza viruses. In especially preferred aspects of the inventive subject matter, compounds were identified using a first-pass in-silico screening approach that bound with high affinity and specificity to the UTR sequences of influenza viruses, and candidate compounds were further evaluated for in vitro antiviral activity using a cell-based reporter assay system. Further compounds were identified using a secondary screen based on validated first screen compounds.

In one aspect of the inventive subject matter, the inventors contemplate a pharmaceutical composition that includes a pharmaceutically acceptable carrier in combination with a compound according to Formula I Formula I wherein A and D are independently optionally substituted aryl or heteroaryl, or D is H or alkyl, and wherein the quinoline moiety is optionally substituted with a halogen, and wherein the compound is present in the composition in an amount effective to reduce viral propagation of a virus belonging to the family of an orthomyxoviridae (and especially influenza virus) when the composition is administered to a person in need thereof.

In especially preferred aspects, A is phenyl or pyridinyl, optionally substituted with alkyl or alkoxy, and/or D is H, alkyl, quinoxalinyl, isoxazolyl, thiazolyl, pyrimidinyl, or dihydropyrrolyl, optionally substituted with alkyl or alkoxy. Therefore, especially contemplated compounds include N-{3-[(4,5-dihydro-3H-pyrrol-2-yl)sulfamoyl]phenyl}-2-(pyridin-3-yl)quinoline-4-carboxamide, 2-(4-methylphenyl)-N-{4-[(pyrimidin-2-yl)sulfamoyl]phenyl}quinoline-4-carboxamide, 6-chloro-N-[4-(piperidin-1-ylcarbonyl)phenyl]-2-(pyridin-4-yl)quinoline-4-carboxamide, 2-phenyl-N-{4-[(1,3-thiazol-2-yl)sulfamoyl] phenyl}quinoline-4-carboxamide, N-[4-(tert-butylsulfamoyl)phenyl]-2-(pyridin-2-yl)quinoline-4-carboxamide, 6-chloro-N-{4-[(5-methyl-1,2-oxazol-3-yl)sulfamoyl]phenyl}-2-(pyridin-3-yl)quinoline-4-carboxamide, N-(4-(N-(quinoxalin-2-yl)sulfamoyl)phenyl)-2-(p-tolyl)quinoline-4-carboxamide, N-(4-(N-(5-methylisoxazol-3-yl)sulfamoyl)phenyl)-2-phenylquinoline-4-carboxamide, N-(4-(N-methylsulfamoyl)phenyl)-2-phenylquinoline-4-carboxamide, 2-(pyridin-4-yl)-N-(4-(N-(thiazol-2-yl)sulfamoyl) phenyl)quinoline-4-carboxamide, 2-(4-methoxyphenyl)-N-(4-(N-(thiazol-2-yl) sulfamoyl)phenyl)quinoline-4-carboxamide, 2-(benzo[d][1,3]dioxol-5-yl)-N-(4-(N-(pyrimidin-2-yl)sulfamoyl)phenyl)quinoline-4-carboxamide, and 2-(3-methoxyphenyl)-1-oxo-N-(4-sulfamoylphenyl)-1,2-dihydroisoquinoline-4-carboxamide.

Viewed from another perspective, the inventors also contemplate a pharmaceutical composition that includes a pharmaceutically acceptable carrier and a compound selected form the group consisting of N-{3-[(4,5-dihydro-3H-pyrrol-2-yl)sulfamoyl]phenyl}-2-(pyridin-3-yl)quinoline-4-carboxamide (A0242), N-{3-[4-(4-acetamido-2-fluorophenyl)-1,3-thiazol-2-yl]phenyl}cyclopropanecarboxamide (A0251), (3R)-1-{[3-(1-benzofuran-2-yl)-1H-pyrazol-4-yl]methyl}-3-[(1-methylimidazol-2-yl)carbonyl]piperidine (A252),(4S)-2-amino-7-methyl-5-oxo-4-phenyl-6-(pyridin-3-ylmethyl)-4H-pyrano[3,2-c]pyridine-3-carbonitrile (A253),N-[3-(4-{[(2,3-difluorophenyl)methyl]amino}piperidin-1-yl)phenyl]pyridine-3-carboxamide (A254),2-bromo-N-(5-{[4-(4-fluorophenyl)piperazin-1-yl]carbonyl}-2-[(1S,9R)-6-oxo-7,11-diazatricyclo[7.3.1.0^{2,7}]trideca-2,4-dien-11-yl]phenyl)benzamide (A256), 2-(4-methylphenyl)-N-{4-[(pyrimidin-2-yl)sulfamoyl] phenyl}quinoline-4-carboxamide (A257), 6-chloro-N-[4-(piperidin-1-ylcarbonyl)phenyl]-2-(pyridin-4-yl)quinoline-4-carboxamide (A258), 2-phenyl-N-{4-[(1,3-thiazol-2-yl)sulfamoyl]phenyl}quinoline-4-carboxamide (A259), N-[4-(tert-butylsulfamoyl)phenyl]-2-(pyridin-2-yl)quinoline-4-carboxamide (A260), 6-chloro-N-{4-[(5-methyl-1,2-oxazol-3-yl)sulfamoyl]phenyl}-2-(pyridin-3-yl)quinoline-4-carboxamide (A263), N-(4-(N-(quinoxalin-2-yl)sulfamoyl)phenyl)-2-(p-tolyl)quinoline-4-carboxamide (A0796), N-(4-(N-(5-methylisoxazol-3-yl)sulfamoyl)phenyl)-2-phenylquinoline-4-carboxamide (A800), N-(4-(N-methylsulfamoyl)phenyl)-2-phenylquinoline-4-carboxamide (A802), 2-(pyridin-4-yl)-N-(4-(N-(thiazol-2-yl)sulfamoyl) phenyl)quinoline-4-carboxamide (A843), 2-(4-methoxyphenyl)-N-(4-(N-(thiazol-2-yl)sulfamoyl)phenyl)quinoline-4-carboxamide (A1004), 2-(benzo[d][1,3]dioxol-5-yl)-N-(4-(N-(pyrimidin-2-yl) sulfamoyl)phenyl)quinoline-4-carboxamide (A1005), 6-(2,5-dimethylthiophen-3-yl)-3-methyl-N-(4-(N-methylsulfamoyl)phenyl)isoxazolo[5,4-b]pyridine-4-carboxamide (A1006), 1-phenyl-N-(4-sulfamoylphenyl)-3-(thiophen-2-yl)-1H-pyrazole-4-carboxamide (A1007), 2-(3-methoxyphenyl)-1-oxo-N-(4-sulfamoylphenyl)-1,2-dihydroisoquinoline-4-carboxamide (A1008), and N-(2-hydroxy-1H-benzo[d]imidazol-6-yl)-2-(pyridin-3-yl)quinoline-4-carboxamide (A1009), wherein the compound is present in the composition in an amount effective to reduce viral propagation of a virus belonging to the family of an orthomyxoviridae (and especially Influenza virus) when the composition is administered to a person in need thereof.

Consequently, the inventors also contemplate an RNA-ligand complex comprising an RNA that is non-covalently bound to a compound according to Formula I or a compound as listed above. Most typically, the RNA will be present in a tetrahelical structure when the compound is bound to the RNA, and/or the complex is disposed in a cell infected with an RNA virus.

Therefore, the inventors also contemplate a method of reducing viral replication in a cell infected with an RNA virus (and especially an Influenza virus), wherein the method includes at least a step of exposing the cell to a ligand at a concentration effective for the ligand to form a complex with a 5'/3'-UTR sequence of the RNA virus to thereby reduce viral replication. With respect to suitable ligands, the same compounds (optionally as prodrug or metabolite) as presented above are especially preferred. Moreover, it is typically preferred that the step of exposing the cell is performed in vivo, and/or that the compound is 2-phenyl-N-{4-[(1,3-thiazol-2-yl)sulfamoyl] phenyl}quinoline-4-carboxamide (A0259).

In another aspect of the inventive subject matter, the inventors also contemplate a method of identifying a viral replication inhibitor for an RNA virus. In such methods, a secondary structure is modeled for an RNA promoter sequence of the RNA virus using an in silico modeling system, and a ligand is identified in silico that binds to the secondary structure using a docking algorithm.

Most typically, the secondary structure comprises a double stranded RNA, a stem-loop structure, or a tetrahelical structure, and it is generally preferred that contemplated methods further include a step of validating binding of the ligand in vitro, and/or a further step of identifying ligand binding features for the validated ligand, followed by an in silico secondary search using the identified ligand features to thereby identify energetically favorable conformers for the identified ligand.

Various objects, features, aspects and advantages of the inventive subject matter will become more apparent from the following detailed description of preferred embodi-

BRIEF DESCRIPTION OF THE DRAWING

FIG. 5A-5G illustrates exemplary results (5A-5C photographs of hemagglutination assay and graph for IC50 data; 5D-5G IC50 data only) for selected compounds.

DETAILED DESCRIPTION

Figure 1:
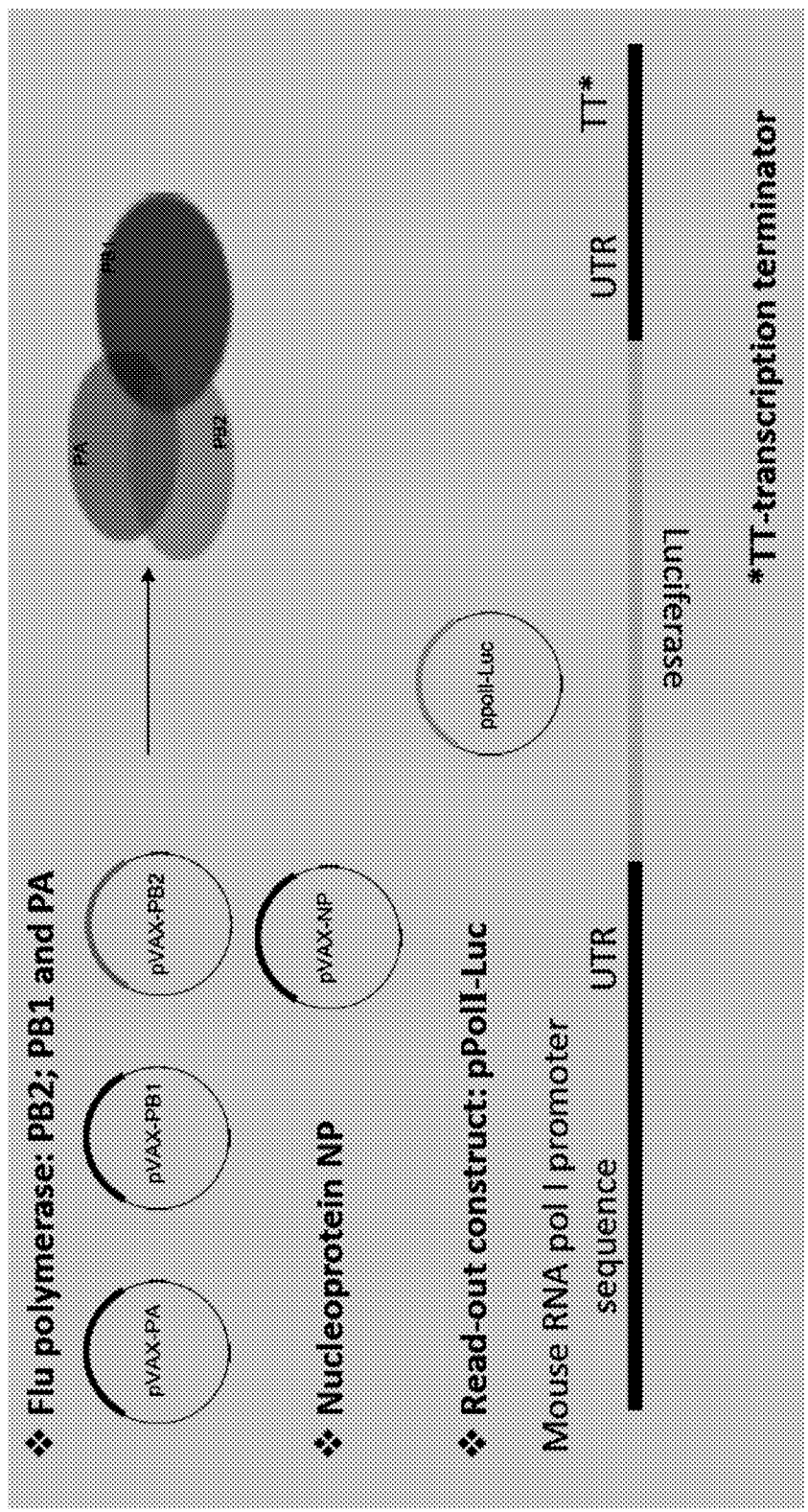
FIG. 1 is a schematic of an Influenza A reporter assay construct

The inventors have discovered that an in-silico screening approach using the influenza viral promoter as bait can be effectively used to identify compounds that specifically bind to the influenza UTR sequences. While in-silico screening of viral RNA is highly problematic in most cases due to generally dynamic nature of RNA, the influenza viral promoter provides a unique and double stranded RNA structure that appears structurally relatively confined. Consequently, using the influenza viral promoter as bait in an in-silico screening approach allowed to rapidly identify potential inhibitors with significant specificity to influenza viruses, and especially influenza A viruses (including seasonal, pandemic, and emerging). Potential hits were then validated in a cell-based model following previously reported methods (see e.g., U.S. Pat. No. 8,633,198).

In especially preferred aspects of the inventive subject matter, several compounds were identified and further evaluated for antiviral activity using a cell-based reporter assay system. Of these compounds, one compound (A0259) particularly demonstrated specific inhibition in the reporter assay without impacting a non-specific reporter system. Furthermore, A0259 also demonstrated direct antiviral activity against actively replicating influenza A virus.

Therefore, and viewed from another perspective, the present inventive subject matter is drawn to antiviral compounds, compositions, and methods, and especially to compositions that include an Influenza A inhibitor that are effective in reducing viral replication in vitro and in vivo. Most advantageously, inhibitors contemplated herein will be specific to RNA viruses, and especially to the Influenza A virus and viruses that are similar to the Influenza A virus (e.g., various orthomyxoviridae, infectious salmon anemia virus).

Based on the assumption that the Influenza A viral promoter structure has a "corkscrew" or "panhandle"-like structure, the inventors identified in silico small molecule inhibitors of the polymerase that are thought to directly interact with the UTRs in the promoter and so inhibit recognition of the promoter structure by its cognate interaction partner, vPol. More specifically, the inventors employed computational modeling utilizing docking software and existing NMR-derived solution structures of the influenza A UTRs.

As a result, the inventors identified certain candidate compounds (Table 1, experiments below), which were predicted to interact with the panhandle structure in the vicinity of A11 (adenosine position 11, see PNAS (2001) 98, No. 19, pp 10602-10607), and hence should possess antiviral activity in the influenza A system. To further evaluate the antiviral activity of the computationally-derived candidates, the compounds were tested side-by-side in a NS 1-enhanced influenza A assay and an irrelevant promoter-containing cell-based reporter assays. The most dramatic inhibition of the influenza reporter system with the concomitant smallest impact on a non-specific promoter was produced by compound A0259 as is further described in more detail below.

Based on these results, a second round of in-silico screening was performed using Phase software to rapidly identify commercially available compounds which share major structural similarities with A0259 within a library of 2 million compounds. Using this strategy, additional compounds with variations of two major substituents around the core A0259 structure were identified and tested (see Table 2 experiments below). These compounds were selected based on the structure of the docked complex between the target RNA and A0259 to define critical binding features of the ligand. These include: hydrogen bond donor groups, such as amide hydrogens; hydrogen bond acceptors, such as carbonyl oxygen and sulfate groups, as well as features providing the overall structure, such as the core aromatic structure. In addition, the RNA structure was used to define excluded volumes, constraining matching ligands to the boundaries of the binding site.

Therefore, it should be appreciated that in silico screening for RNA promoter inhibitors is a valid tool for drug discovery. Indeed, the herein presented methods yielded eleven hits with potential antiviral activity, of which one compound in particular (A0259) had significant antiviral activity both in a reporter system and in a live infection assay. A second computational evaluation identified additional A0259-related compounds with antiviral activity. The concept of utilizing computational modeling to rapidly identify small molecule inhibitors of viral replication by targeting stable and unusual nucleic acid sequences is also thought to be applicable to other RNA viruses including but not limited to measles, mumps, rabies, HCV, and respiratory syncytial virus (RSV), retroviruses, and perhaps even DNA viruses.

Contemplated Compounds

Based at least on the selected hits and structural information for the promoter structure, the inventors contemplate that suitable small molecule inhibitors of Influenza A will generally have a structure according to Formula Ia

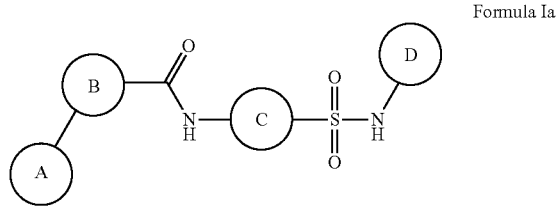

Formula Ia wherein A, C, and D are independently optionally substituted aryl or heteroaryl, and B is an optionally substituted fused aryl or fused heteroaryl. Moreover, it should be appreciated that the amide group connecting B and C and/or the sulfonamide group connecting C and D may be suitably modified or replaced, so long as the modified or replaced group(s) will provide at least one of a hydrogen bond donor and acceptor group, and optionally provide a rotational barrier under physiological conditions.

In other aspects of the invention, preferred contemplated compounds will have a structure according to Formula I

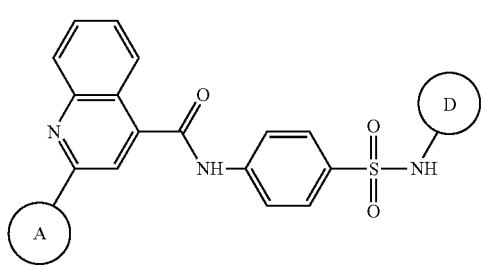

Formula Ib wherein A and D are independently optionally substituted aryl or heteroaryl, or D is H or alkyl, and wherein the quinoline moiety is optionally substituted with a halogen.

For example, suitable (optionally substituted) aryl or heteroaryl groups include aromatic monocyclic or polycyclic groups, typically comprising between 5 and 18 carbon ring members, which may be unsubstituted or substituted by one or more suitable substituents as defined herein, and to which may be fused one or more cycloalkyl groups, heterocycloalkyl groups, or heteroaryl groups, which themselves may be unsubstituted or substituted by one or more suitable substituents. Thus, the term "aryl group" includes a benzyl group (Bzl). Examples include phenyl, biphenyl, 1,2,3,4-tetrahydronaphthyl, naphthyl, anthryl, and phenanthryl. Suitable heteroaryl groups will typically include aromatic monocyclic or polycyclic groups comprising generally between 4 and 18 ring members, including 1-5 heteroatoms selected from nitrogen, oxygen, and sulfur, which may be unsubstituted or substituted by one or more suitable substituents as defined below, and to which may be fused one or more cycloalkyl groups, heterocycloalkyl groups, or aryl groups, which themselves may be unsubstituted or substituted by one or more suitable substituents. Examples include thienyl, furanyl, thiazolyl, triazolyl, imidazolyl, isoxazolyl, oxadiazolyl, tetrazolyl, pyridyl, pyrrolyl, thiadiazolyl, oxadiazolyl, oxathiadiazolyl, thiatriazolyl, pyrimidinyl, isoquinolinyl, quinolinyl, napthyridinyl, phthalimidyl, benzimidazolyl, and benzoxazolyl.

In general, the various moieties or functional groups for variables in the formulae may be substituted by one or more suitable "substituents". The term "substituent" or "suitable substituent" is intended to mean any suitable substituent that may be recognized or selected, by those skilled in the art. Illustrative examples of useful substituents are those found in the exemplary compounds that follow, as well as halogen (chloro, iodo, bromo, or fluoro); $C_{1-6}$-alkyl; $C_{1-6}$-alkenyl; $C_{1-6}$-alkynyl; hydroxyl; $C_{1-6}$ alkoxyl; amino; nitro; thiol; thioether; imine; cyano; amido; phosphonato; phosphine; carboxyl; carbonyl; aminocarbonyl; thiocarbonyl; sulfonyl; sulfonamine; sulfonamide; ketone; aldehyde; ester; oxygen (=O); haloalkyl (e.g., trifluoromethyl); carbocyclic cycloalkyl, which may be monocyclic or fused or non-fused polycyclic (e.g., cyclopropyl, cyclobutyl, cyclopentyl, or cyclohexyl), or a heterocycloalkyl, which may be monocyclic or fused or non-fused polycyclic (e.g., pyrrolidinyl, piperidinyl, piperazinyl, morpholinyl, or thiazinyl); carbocyclic or heterocyclic, monocyclic or fused or non-fused polycyclic aryl (e.g., phenyl, naphthyl, pyrrolyl, indolyl, furanyl, thiophenyl, imidazolyl, oxazolyl, isoxazolyl, thiazolyl, triazolyl, tetrazolyl, pyrazolyl, pyridinyl, quinolinyl, isoquinolinyl, acridinyl, pyrazinyl, pyridazinyl, pyrimidinyl, benzimidazolyl, benzothiophenyl, or benzofuranyl); amino (primary, secondary, or tertiary); nitro; thiol; thioether, O-lower alkyl; O-aryl; aryl; aryl-lower alkyl; $CO_2CH_3$; $CONH_2$; $OCH_2CONH_2$; $NH_2$; $SO_2NH_2$; $OCHF_2$; $CF_3$; $OCF_3$; and the like. Such moieties may also be optionally substituted by a fused-ring structure or bridge, for example $OCH_2$—O.

All of these substituents may optionally be further substituted with a substituent selected from groups such as hydroxyl groups, halogens, oxo groups, alkyl groups, acyl groups, sulfonyl groups, mercapto groups, alkylthio groups, alkyloxyl groups, cycloalkyl groups, heterocycloalkyl groups, aryl groups, heteroaryl groups, carboxyl groups, amino groups, alkylamino groups, dialkylamino groups, carbamoyl groups, aryloxyl groups, heteroaryloxyl groups, arylthio groups, heteroarylthio groups, and the like. The term "optionally substituted" is intended to expressly indicate that the specified group is unsubstituted or substituted by one or more suitable substituents, unless the optional substituents are expressly specified, in which case the term indicates that the group is unsubstituted or substituted with the specified substituents. As defined above, various groups may be unsubstituted or substituted (i.e., they are optionally substituted) unless indicated otherwise herein (e.g., by indicating that the specified group is unsubstituted).

It should further be appreciated that contemplated compounds will include those that can be identified in an in silico approach as described above and/or an inhibition assay as exemplarily shown in FIG. 1. Most preferably, such compounds will have an IC50 of equal or less than 10 µM, even more preferably of equal or less than 1 µM, and most preferably of equal or less than 100 nM, and will have no apparent toxicity at the $IC_{50}$ as measured above. Once candidate compounds (typically having $IC_{50}$ of equal or less than 10 µM) are identified, such compounds can be further modified to ascertain SAR and to produce compounds with higher potency, reduced toxicity, and/or increased bioavailability. Therefore, particularly preferred compounds not only include those as shown in Formulae Ia and Ib above, but also include those of Tables 2 and 3 as described in further detail below.

Furthermore it should be noted that the compounds contemplated herein may be prepared as prodrugs. The term "prodrug" as used herein refers to a modification of contemplated compounds, wherein the modified compound exhibits less pharmacological activity (as compared to the modified compound) and wherein the modified compound is converted within a target cell (e.g., B-cell) or target organ/anatomic structure (e.g., joint) back into the modified form. For example, conversion of contemplated compounds into prodrugs may be useful where the active drug is too toxic for safe systemic administration, or where the contemplated compound is poorly absorbed by the digestive tract or other compartment or cell, or where the body breaks down the contemplated compound before reaching its target. Thus, it should be recognized that the compounds according to the inventive subject matter can be modified in numerous manners, and especially preferred modifications include those that improve one or more pharmacokinetic and/or pharmacodynamic parameter. For example, one or more substituents may be added or replaced to achieve a higher AUC in serum.

On the other hand, and especially where increased solubility is desired, hydrophilic groups may be added. Still further, where contemplated compounds contain one or more bonds that can be hydrolyzed (or otherwise cleaved), reaction products are also expressly contemplated. Exemplary suitable protocols for conversion of contemplated compounds into the corresponding prodrug form can be found in "Prodrugs (Drugs and the Pharmaceutical Sciences: a Series of Textbooks and Monographs)" by Kenneth B. Sloan (ISBN: 0824786297), and "Hydrolysis in Drug and Prodrug Metabolism: Chemistry, Biochemistry, and Enzymology" by Bernard Testa, Joachim M. Mayer (ISBN: 390639025X), both of which are incorporated by reference herein. Moreover, especially where contemplated compounds have a higher activity when the compound is metabolized (e.g., hydrolyzed, hydroxylated, glucuronidated, etc.), it should be appreciated that metabolites of contemplated compounds are also expressly contemplated herein.

Additionally, it is contemplated that contemplated compounds may be combined (in vivo or in a pharmaceutical formulation or administration regimen) with at least one other pharmaceutically active ingredient, and especially contemplated other ingredients include various antiviral drugs (e.g., as described in U.S. Pat. No. 8,633,198), various immunomodulatory drugs, and/or anti-inflammatory drugs (e.g., steroids and NSAIDS), etc. Concentrations of second pharmaceutically active ingredients are typically at or preferably below those recommended for stand-alone administration, however, higher concentrations are also deemed suitable for use herein.

Therefore, contemplated pharmaceutical compositions will especially include those in which contemplated compounds (and additional pharmaceutically active ingredients) are provided with a suitable pharmaceutically acceptable carrier, wherein contemplated compounds are preferably present at a concentration effective to reduce viral propagation in an organism and/or target organ to a degree effective to reduce and more preferably to treat signs and symptoms of a disease associated with the viral infection. Viewed from a different perspective, contemplated compounds are present in a composition in an amount effective to treat a viral infection, and especially a viral infection with an RNA virus (and particularly influenza virus).

For example, virus infections suitable for treatment with contemplated compounds (and especially A0259) are those produced by infection with an RNA virus (and especially a negative stranded RNA virus), and particularly those viruses bearing the closest resemblance to influenza A. Thus, contemplated viruses include influenza B, and influenza virus C. Phylogenetically related additional viruses suitable for treatment with contemplated compounds include mononegavirales family which includes paramyxoviridae [including Newcastle disease virus; Hendra virus; Nipah virus; rinderpest virus; measles virus; Sendai virus; bovine parainfluenza virus 3; human parainfluenza viruses 1 and 3; mumps virus; parainfluenza viruses 2, 4a, and 4b; metapneumovirus; respiratory syncytial virus], rhabdoviridae [including the mammalian infective vesicular stomatitis virus and rabies virus; the plant infective Strawberry crinkle cytorhabdovirus, lettuce necrotic yellows virus, *Cynodon* chlorotic streak virus, Maize mosaic virus, Northern cereal mosaic virus, Orchid fleck virus, Rice yellow stunt virus, *Sonchus* yellows net virus, and Taro vein chlorosis virus; the fish infective Hirame rhabdovirus, infectious hematopoietic necrosis virus, viral hemorrhagic septicemia virus, and Snakehead virus as well as bovine ephemeral fever virus and Adelaide River virus]; the filoviridae [including the hemorrhagic ebolavirus and Marburg viruses] and bornavirus. While the inventors do not have actual data in support of potential activity against these viruses, it should be noted that an in silico and/or RSV-based expression system can be used to determine susceptibility of these viruses, and that such system can be prepared by the PHOSITA without undue experimentation.

Depending on the particular use and structure, it is therefore contemplated that the compounds according to the inventive subject matter are present in the composition in an amount between 1 microgram to 1000 milligram, more typically between 10 microgram to 500 milligram, and most typically between 50 microgram to 500 milligram per single dosage unit. Thus, preferred concentrations of contemplated compounds in vivo or in vitro will generally be between 0.1 nM and 500 microM, more typically between 50 nM and 400 microM, and most typically between 100 nM and 200 microM.

Furthermore, it should be recognized that all formulations are deemed suitable for use herein and especially include oral and parenteral formulations. For example, for oral administration, contemplated compositions may be in the form of a tablet, capsule, suspension, or liquid. The pharmaceutical composition is preferably made in the form of a dosage unit containing a particular amount of the active ingredient. Examples of such dosage units are tablets or capsules. The active ingredient may also be administered by injection as a composition wherein, for example, saline, dextrose or water may be used as a suitable carrier. In especially preferred aspects, it is contemplated that the formulation is suitable for topical administration, administration via aerosol, and for intrathecal administration. Consequently, especially suitable formulations may be sterile aqueous solutions for topical spray or drop administration, or application as a tincture. Alternatively, suitable topical formulations include creams, ointments, foams, lotions, emulsions, etc. Furthermore, where the compound is formulated for intrathecal administration (e.g., in the treatment of spinal cord injury), it is preferred that the compound is prepared as an injectable solution, suspension, or emulsion. In still further contemplated formulations, contemplated compounds may be formulated for aerosol delivery (e.g., micropowderized, coated onto a dispersible carrier, dissolved in atomizable solvent, etc.)

It should be appreciated that the choice of the particular formulation and carrier will at least in part depend on the specific use and type of compound. There are numerous manners of drug formulation known in the art, and all of those are deemed suitable for use herein (see e.g., Pharmaceutical Preformulation and Formulation: A Practical Guide from Candidate Drug Selection to Commercial Dosage Form by Mark Gibson; Informa HealthCare, ISBN: 1574911201; or Advanced Drug Formulation Design to Optimize Therapeutic Outcomes by Robert O. Williams, David R. Taft, and Jason T. McConville; Informa HealthCare; ISBN: 1420043870).

The amount of therapeutically active compound that is administered and the dosage regimen for treating a disease condition with the compounds and/or compositions of this invention depends on a variety of factors, including the age, weight, sex and medical condition of the subject, the severity of the disease, the route and frequency of administration, and the particular compound employed, and thus may vary widely. However, especially suitable quantities are provided above, and may therefore allow for a daily dose of about 0.001 (or even less) to 100 mg/kg body weight, preferably between about 0.01 and about 50 mg/kg body weight and most preferably from about 0.1 to 20 mg/kg body weight. Typically, a daily dose can be administered in one to four doses per day.

For therapeutic or prophylactic purposes, contemplated compounds are ordinarily combined with one or more excipients appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of active compound in hydroxypropyl-methyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The compounds may be dissolved in water, polyethylene glycol, propylene glycol, ethanol, corn oil, cottonseed oil, peanut oil, sesame oil, benzyl alcohol, sodium chloride, and/or various buffers. Other excipients and modes of administration are well and widely known in the pharmaceutical art.

Experimental Data and Results

Computational Hit Identification Studies:

As the starting point for the in silico analysis, the inventors used experimentally determined solution structures of the panhandle RNA. These had been previously obtained by NMR spectroscopy and deposited in the Protein Data Bank (PDB). The PDB identification code of the relevant set of structural data is 1JO7. Since NMR structure is solved as an ensemble of conformations existing in solution, the inventors chose three representatives sufficiently different from each other to allow for a broad coverage of the conformational space.

With the target structures selected, the inventors used molecular docking to screen an in-house virtual library of commercially available compounds, which contained about 5 million chemical compounds at the time of the screen. The inventors selected a subset of the database content that had physico-chemical properties most consistent with the potential binding site on the surface of the RNA. Compounds were filtered by flexibility (no more than 8 rotatable bonds), log P (between 0 and 5), presence of hydrogen bond donors and total heteroatom count (2 and 12, respectively), as well as molecular weight (excluding compounds smaller than 300 Da). The total size of the subset to be docked was about 300,000 compounds. In the process of setup, the inventors specifically targeted the binding site of the RNA polymerase at the bases A10 and A11 in the NMR structure. This region of RNA has a notable set of cavities in the otherwise smooth double-helical structure, and thus can be targeted by compounds that would not bind the regular RNA or DNA.

From the computationally generated set of 2,000 compounds, eleven were selected for further evaluation and purchased from commercial suppliers. Table 1 below depicts selected hits from the computational screen along with the corresponding structures.

TABLE 1

A0242: N-{3-[(4,5-dihydro-3H-pyrrol-2-yl)sulfamoyl]phenyl}-2-(pyridin-3-yl)quinoline-4-carboxamide

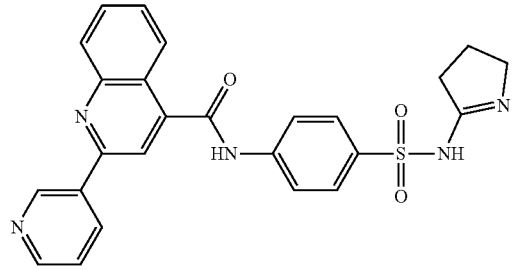 [SMILES: O=C(Nc1ccc(S(=O)(=O)NC2=NCCC2)cc1)c1cc(-c2cccnc2)nc2ccccc12]

A0251: N-{3-[4-(4-acetamido-2-fluorophenyl)-1,3-thiazol-2-yl]phenyl}cyclopropanecarboxamide

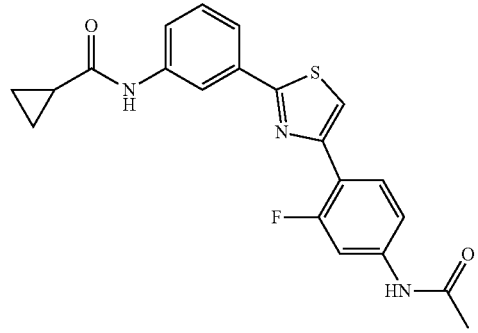 [SMILES: CC(=O)Nc1ccc(-c2csc(-c3cccc(NC(=O)C4CC4)c3)n2)c(F)c1]

A0252: (3R)-1-{[3-(1-benzofuran-2-yl)-1H-pyrazol-4-yl]methyl}-3-[(1-methylimidazol-2-yl)carbonyl]piperidine

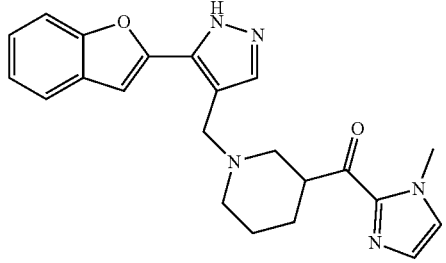 [SMILES: Cn1ccnc1C(=O)C1CCCN(Cc2cn[nH]c2-c2cc3ccccc3o2)C1]

A0253: (4S)-2-amino-7-methyl-5-oxo-4-phenyl-6-(pyridin-3-ylmethyl)-4H-pyrano[3,2-c]pyridine-3-carbonitrile

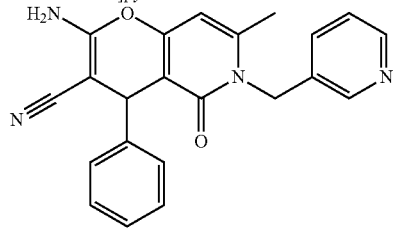

A0254: N-[3-(4-{[(2,3-difluorophenyl)methyl]amino}piperidin-1-yl)phenyl]pyridine-3-carboxamide

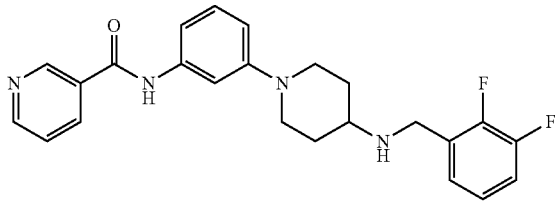 [SMILES: O=C(Nc1cccc(N2CCC(NCc3cccc(F)c3F)CC2)c1)c1cccnc1]

TABLE 1-continued

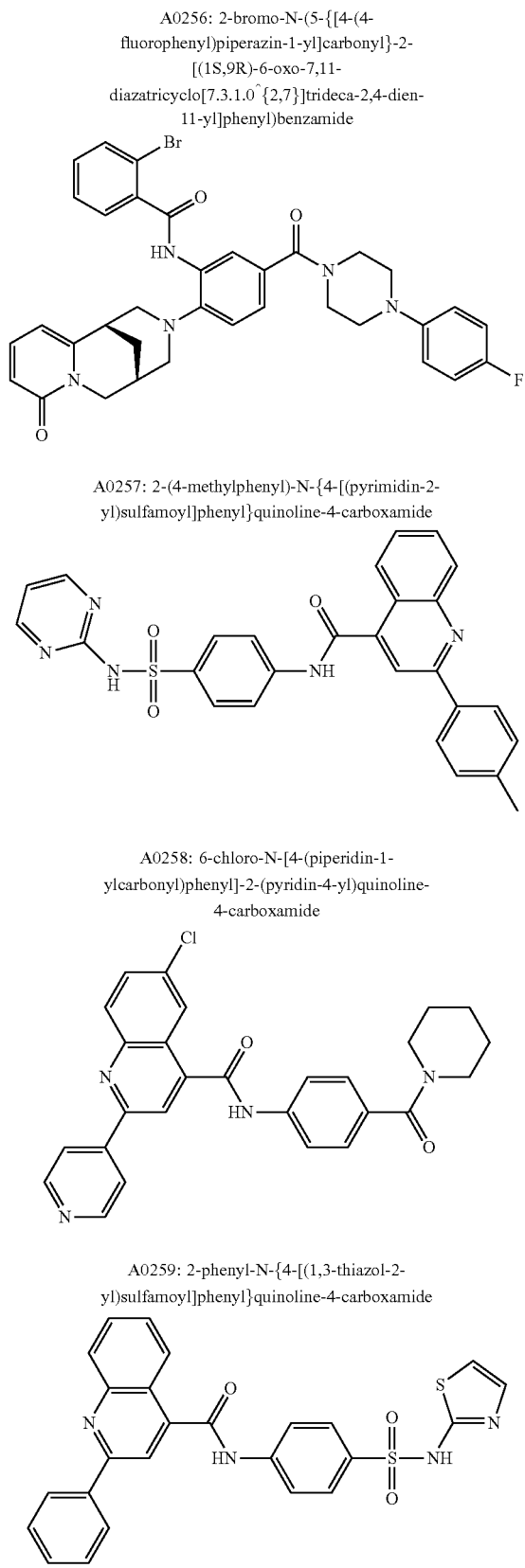

A0256: 2-bromo-N-(5-{[4-(4-fluorophenyl)piperazin-1-yl]carbonyl}-2-[(1S,9R)-6-oxo-7,11-diazatricyclo[7.3.1.0^{2,7}]trideca-2,4-dien-11-yl]phenyl)benzamide A0257: 2-(4-methylphenyl)-N-{4-[(pyrimidin-2-yl)sulfamoyl]phenyl}quinoline-4-carboxamide A0258: 6-chloro-N-[4-(piperidin-1-ylcarbonyl)phenyl]-2-(pyridin-4-yl)quinoline-4-carboxamide A0259: 2-phenyl-N-{4-[(1,3-thiazol-2-yl)sulfamoyl]phenyl}quinoline-4-carboxamide

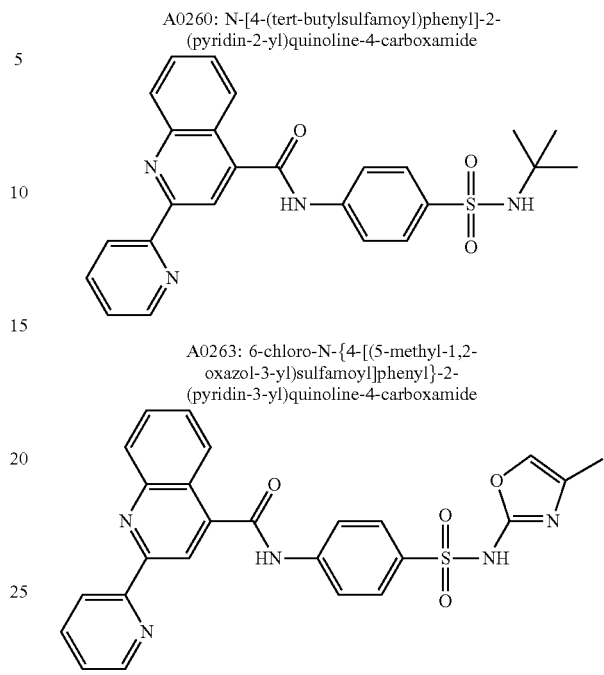

A0260: N-[4-(tert-butylsulfamoyl)phenyl]-2-(pyridin-2-yl)quinoline-4-carboxamide A0263: 6-chloro-N-{4-[(5-methyl-1,2-oxazol-3-yl)sulfamoyl]phenyl}-2-(pyridin-3-yl)quinoline-4-carboxamide Cell-Based Reporter Assays:

Previous reports using a plasmid DNA-based transfection scheme have demonstrated that co-expression of the three viral polymerase subunits (PA, PB1, PB2) along with nucleoprotein (NP) and a reporter RNA encoding chloramphenicol acetyl transferase (CAT) flanked by the viral UTRs results in CAT activity. It is important to note that unlike the other transgenes used in this type of assay (i.e., PA, PB1, PB2, and NP) which utilize a RNA polymerase II expression cassette borrowed from the cytomegalovirus promoter, the RNA encoding the reporter gene necessitates the use of an RNA polymerase I expression cassette in order to produce RNAs that are biochemically indistinguishable from those utilized by the influenza virus (i.e., by virtue of having defined 5' and 3' ends, being un-"capped" on the 5' terminus, and free of the RNA polymerase II expression system's poly-adenosine stretch on the 3' terminus).

Figure 2:
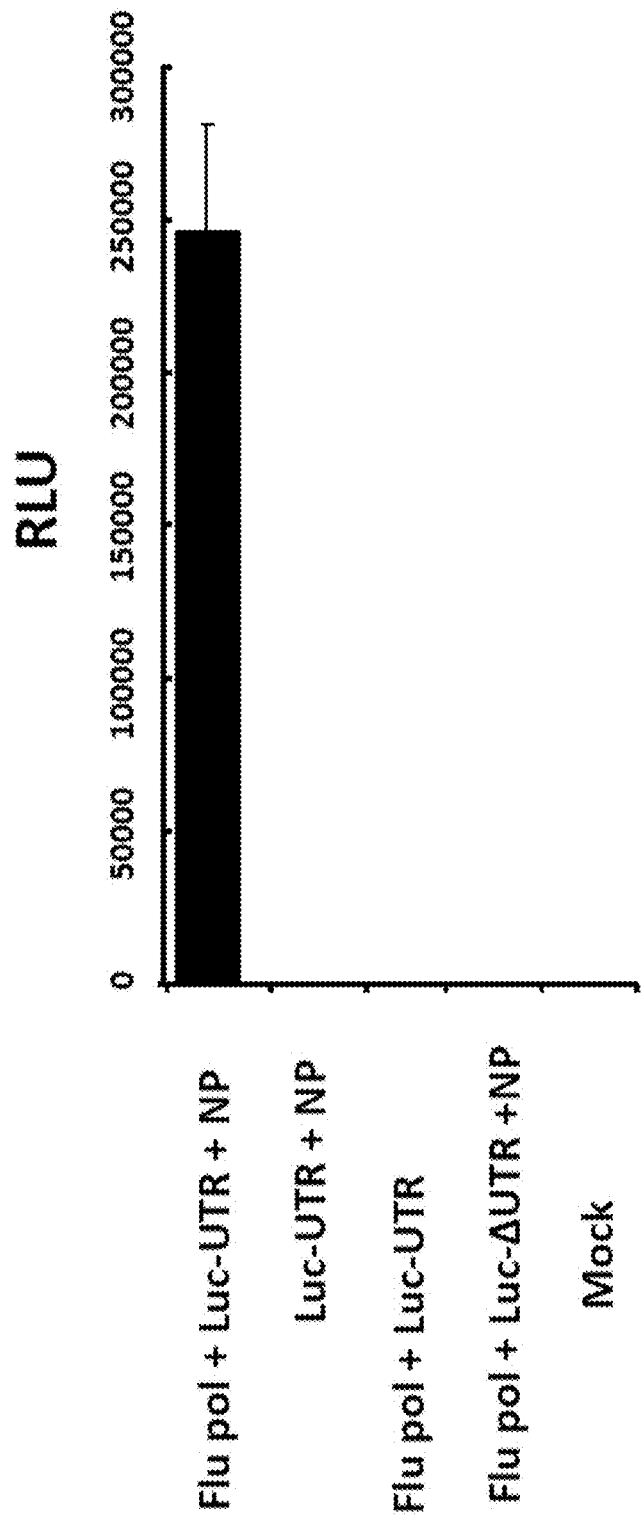
FIG. 2 is a graph indicating requirements of components in a luciferase assay of FIG. 1.

To further adapt a previously established system for drug discovery, the inventors made two modifications. First, the inventors substituted the CAT reporter gene with the firefly luciferase reporter gene to increase signal strength and utilize a broader series of reagents and instruments for signal detection (FIG. 1). To evaluate the efficacy and specificity of this reporter substitution, different sets of plasmids were transfected into the mouse B 16-F10 melanoma cell line. These results demonstrate a robust signal in cells transfected with all five plasmids (e.g., encoding PA, PB 1, PB2, NP, and the RNA polymerase I-driven luciferase RNA construct) but no detectable expression when any of these constituents were removed or in the absence of UTR-based promoter sequences (FIG. 2).

Figure 3:
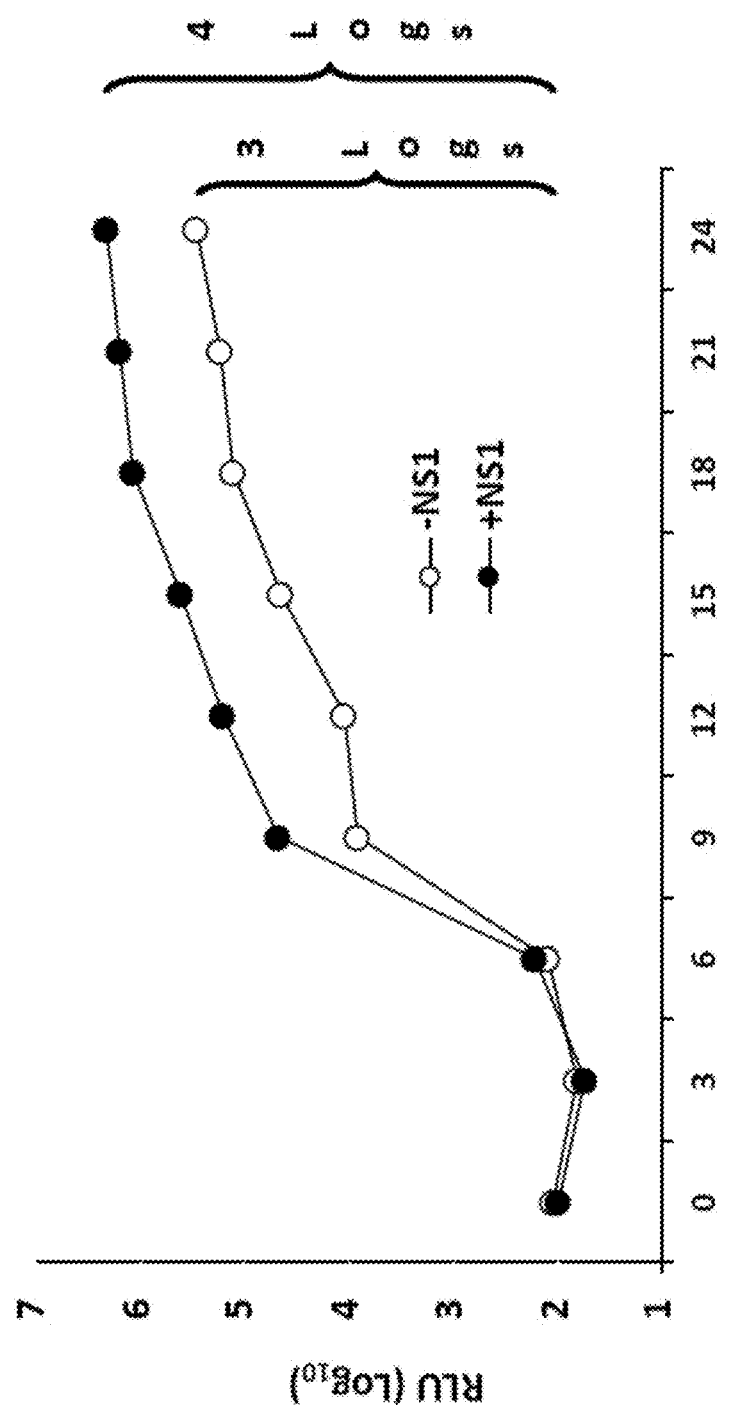
FIG. 3 is a graph depicting exemplary results for enhancement of expression in a luciferase assay.

The second modification to the reporter system was made through the inclusion of a plasmid construct driving the simultaneous expression of the viral non-structural 1 (NS 1) protein. NS 1 mediates a wide variety of functions during viral infection including inhibiting the host cell antiviral response while regulating viral RNA synthesis and enhancing viral protein translation. This modification resulted in an amplification of signal strength by approximately tenfold without altering the background "noise" of the system which enables kinetic analysis to identify optimal drug dosing and harvest schedules (FIG. 3). Here, the graph illustrates that addition and expression of a plasmid encoding NS 1 in addition to the components of FIG. 1 substantially enhances luciferase expression (by about 10-fold). Creation of this assay system allows for the identification of broad classes of entities (be they synthetic small molecules, natural product-derived compounds, nucleic acids, or biologics) that inhibit viral gene expression dependent on any of the viral proteins or RNAs used in the assay (i.e., the corkscrew structure, any of the viral polymerase subunits, NP, and NS 1).

Figure 4A:
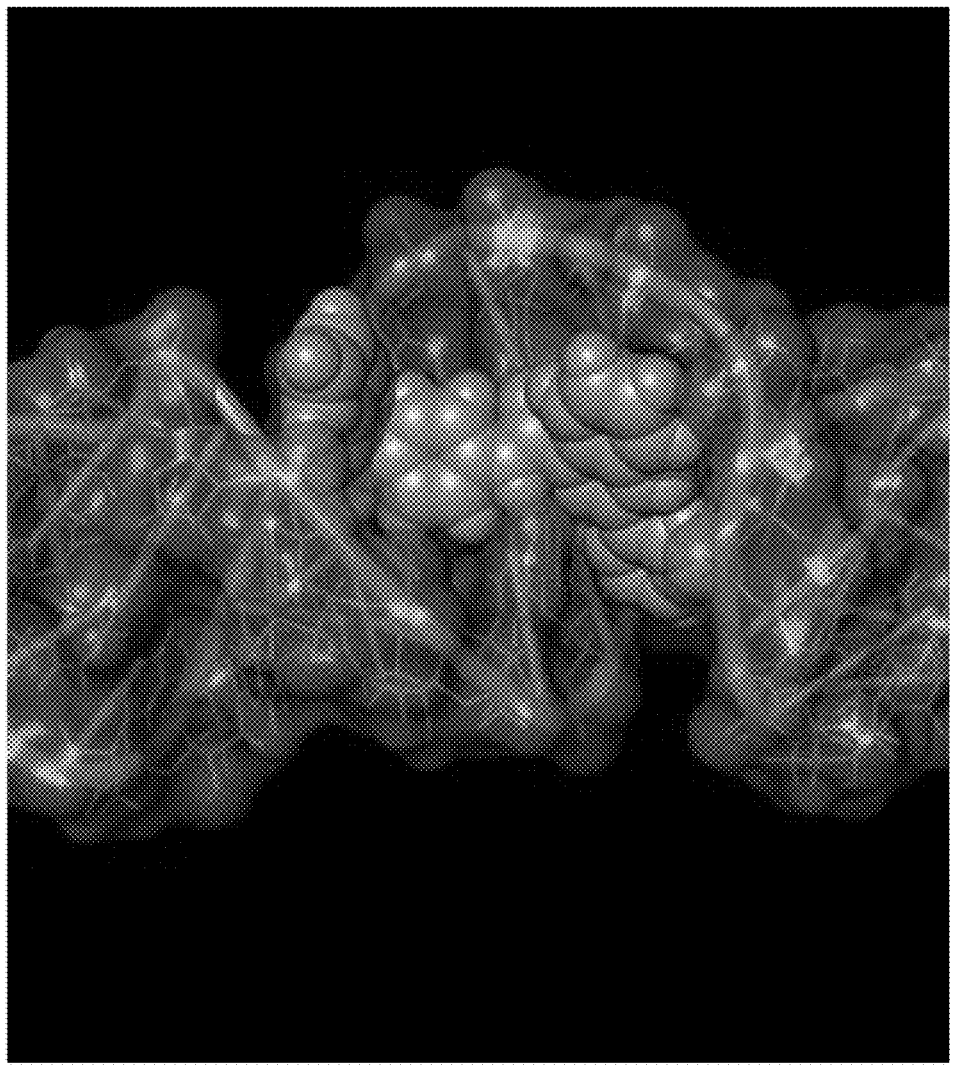
FIG. 4A is a space-fill model depicting the influenza 'panhandle' promoter in complex with A0259.
Figure 4B:
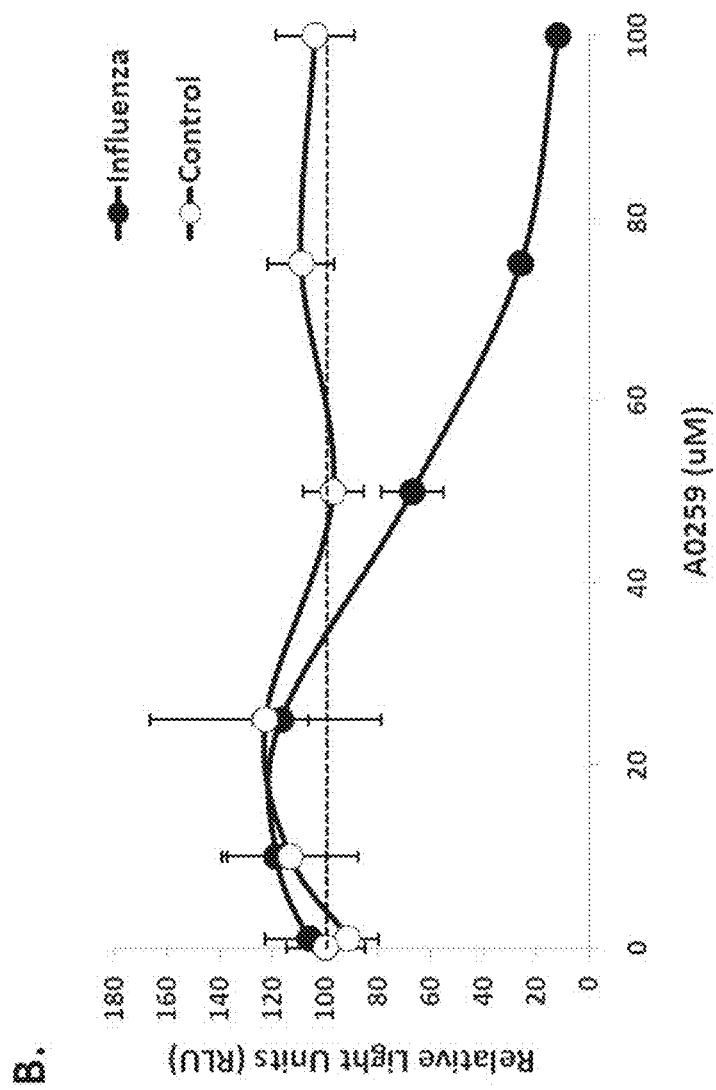
FIG. 4B is a graph depicting a dose response curve and control for A0259.

To evaluate the antiviral activity of the computationally-derived candidate compounds described above, the compounds were tested in side-by-side NS 1-enhanced influenza A and an irrelevant promoter-containing cell-based reporter assays. The most dramatic inhibition of the influenza reporter system with the concomitant smallest impact on a non-specific promoter was produced by compound A0259 (FIG. 4a with accompanying dose response of an influenza A reporter assay system and cell control screen shown in FIG. 4b) although many of the other compounds warrant further investigation in a titration series tested in the reporter assays described.

More specifically, and with further reference to the system of FIG. 1, viral genes encoding PA, PB 1, PB2, NP, and NS 1 were amplified by reverse transcriptase-polymerase chain reaction (or RT-PCR) of a viral cDNA template using gene-specific oligonucleotides. Resulting PCR products were subsequently cloned into a mammalian expression vector and the sequence of the inserts was verified by DNA sequencing. To generate the RNA polymerase I-dependent expression cassette, an RNA polymerase I promoter sequence derived from the 255 bp sequence upstream of the 45S rRNA transcription start site was linked to a multiple cloning site followed by a 33 bp RNA polymerase I termination sequence was generated by PCR using overlapping oligonucleotides and cloned into pBluescript in a similar manner to published reports. This construct, called pPolI, was then digested within the multiple cloning site and directionally ligated to a 5'UTR/luciferase/3'UTR hence generating pPolI-Luc. The pPolI-Luc-DelUTR (i.e., with deleted UTRs) and pPolI-GFP (which possesses UTRs but encodes the green fluorescence protein instead of luciferase) constructs were generated in an analogous fashion.

Transfections were performed using mouse B 16-F10 melanoma cells and a commercially available transfection reagent per the manufacturer's suggestions to confirm the system's activity. Briefly, 2 µg of plasmid (e.g., 400 ng of each of constructs encoding PA, PB 1, PB2, NP, and pPolI-Luc) were complexed with 15 µL of reagent prior to addition to logarithmically dividing melanoma cells. Transfection complexes were removed after four hours and unless otherwise noted, luciferase activity was assayed 20 hours post-transfection. Experiments involving NS 1 were performed in an analogous manner wherein the total amount of plasmid DNA remained fixed at 2 µg but only 333 ng of each plasmid was used due to the need for six plasmids. As a negative/irrelevant control, the inventors also transfected human HEK-293T cells with a DNA construct encoding luciferase driven by the BAX promoter and tested these cells in their response to drug treatment as a potential indicator of non-specific toxicity.

Figure 5A:
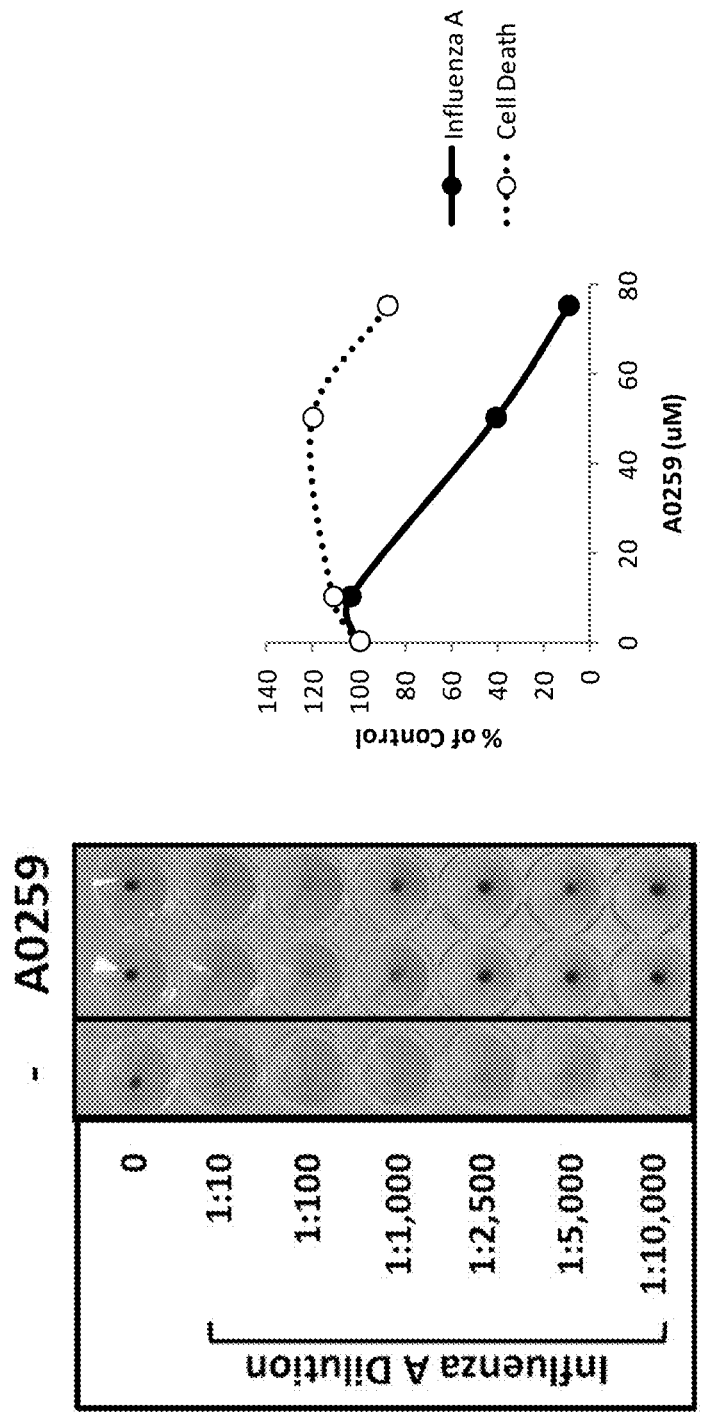
Figure 5B:
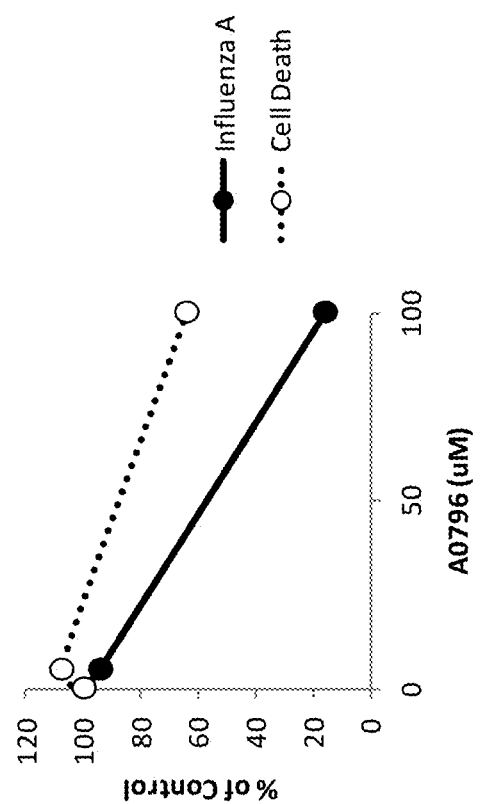
Figure 5C:
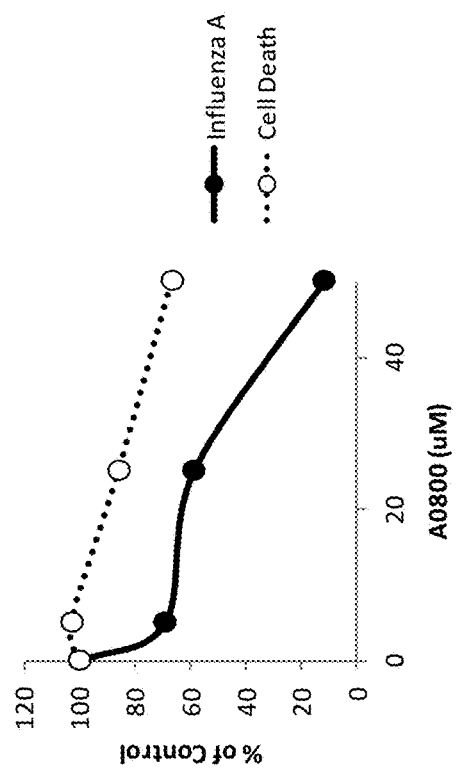

A0259 was further evaluated in its ability to inhibit active influenza A viral proliferation in cell culture because of its successful specific inhibition of the viral reporter system described above. An influenza A/Puerto Rico/8/34 dilution series incubated in the presence of 75 uM A0259 demonstrated that viral dilutions below a thousand-fold from stock were inhibited from successfully replicating in recipient cells as demonstrated by the observance of freely settling cell pellets or "buttons" (FIG. 5A).

Hemagglutination Assay:

Fifty thousand MDCK (ATCC # CCL-34) cells were seeded in a 96-well plate (Becton Dickinson #353072) and grown overnight in Dulbecco's Modified Eagle's Medium: IX, with 4.5 g/L glucose, L-glutamine, and sodium pyruvate (Cellgro 10-013-CV) supplemented with 10% fetal bovine serum (Thermo HyClone SH30910.03) and 1% penicillin-streptomycin-fungizone (Thermo HyClone SV30079.01), which will furthermore be known as DMEM CM. The following day the cells were washed twice with DMEM CM and incubated for two hours at 37° C. with A0259 (75 µM) in DMEM CM. After two hours, the supernatant was aspirated and the cells were washed twice with Dulbecco's Modified Eagle's Medium: IX, with 4.5 g/L glucose, L-glutamine, and sodium pyruvate (Cellgro 10-013-CV) supplemented with 0.2% Bovine Serum Albumin (Sigma-Aldrich #A7906), 25 mM Hepes buffer (Affymetrix #16924), and 2 µg/mL TPCK Trypsin (Thermo Scientific #20233), furthermore known as Influenza Media or IM, and replaced with IM containing a titration of influenza A/Puerto Rico/8/34 virus (ATCC#VR-1469). After the two hour incubation, the supernatant was aspirated and the cells were washed twice with DMEM CM and replaced with DMEM CM containing A0259 (75 µM) and incubated overnight at 37° C. The following day 50 µL of supernatant was removed and re-plated in a 96-well V-bottom plate (Nunc #249662) to which 50 µL of 0.5% Chicken Red Blood Cells (Innovative Research #IC05-0810) was added, mixed, and allowed to sit for 30 minutes prior to photography to assess agglutination activity.

Second Round/Iterative Computational Screens:

As previously mentioned, one of the tested compounds, A0259, demonstrates antiviral activity in the two in vitro assays utilized. Using the chemical structure of A0259 as the starting point, additional searches were performed using quantitative structure-activity relationships (QSAR) software. This approach first defines a set of ligand features important for binding and is commonly referred to as the pharmacophore. Next, the pharmacophore is used to query a pre-generated compound library (representing 2 million commercially available compounds with molecular weights and structural features within the drug-like range) containing all energetically favorable conformers of each compound allowing for a quick comparison of each conformer to the pharmacophore in question.

Selected compounds of that screen are shown in Table 2 below. Table 2 below shows compounds identified based on the structural similarity with A0259 that can be used as further antiviral agents and validated using the in vitro systems described above.

TABLE 2

A0796: (Vitas-M, STK420362) N-(4-(N-(quinoxalin-2-yl)sulfamoyl)phenyl)-2-(p-tolyl)quinoline-4-carboxamide

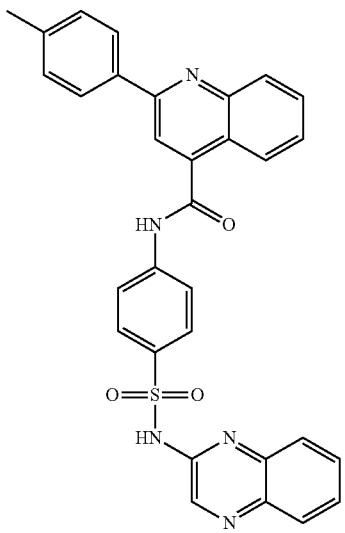 [SMILES: Cc1ccc(-c2cc(C(=O)Nc3ccc(S(=O)(=O)Nc4cnc5ccccc5n4)cc3)c3ccccc3n2)cc1]

A0800: (Vitas-M, STK451721) N-(4-(N-(5-methylisoxazol-3-yl)sulfamoyl)phenyl)-2-phenylquinoline-4-carboxamide

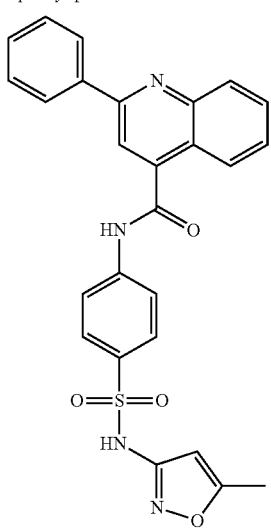

TABLE 2-continued

A0802: (Vitas-M, STK459650) N-(4-(N-methylsulfamoyl)phenyl)-2-phenylquinoline-4-carboxamide

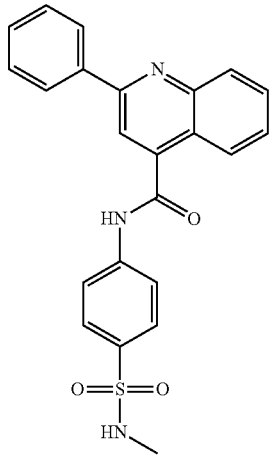 [SMILES: CNS(=O)(=O)c1ccc(NC(=O)c2cc(-c3ccccc3)nc3ccccc23)cc1]

A0843: (Enamine, Z30538327) 2-(pyridin-4-yl)-N-(4-(N-(thiazol-2-yl)sulfamoyl)phenyl)quinoline-4-carboxamide

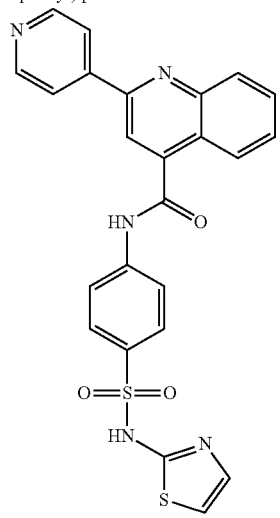

A1004: (Enamine, T5245026) 2-(4-methoxyphenyl)-N-(4-(N-(thiazol-2-yl)sulfamoyl)phenyl)quinoline-4-carboxamide

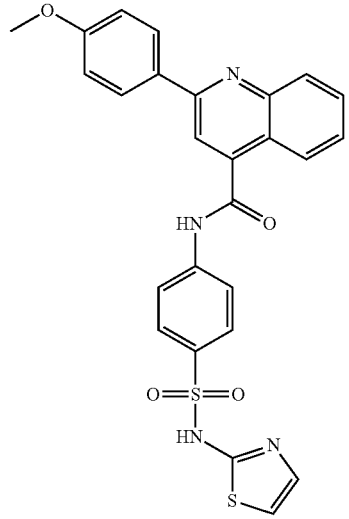 [SMILES: COc1ccc(-c2cc(C(=O)Nc3ccc(S(=O)(=O)Nc4nccs4)cc3)c3ccccc3n2)cc1]

TABLE 2-continued

A1005: (Vitas-M, STK425593) 2-(benzo[d][1,3]dioxol-5-yl)-N-(4-(N-(pyrimidin-2-yl)sulfamoyl)phenyl)quinoline-4-carboxamide

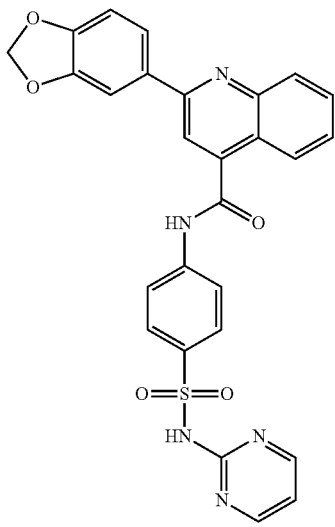 [SMILES: O=C(Nc1ccc(S(=O)(=O)Nc2ncccn2)cc1)c1cc(-c2ccc3c(c2)OCO3)nc2ccccc12]

A1006: (Enamine, Z229954096) 6-(2,5-dimethylthiophen-3-yl)-3-methyl-N-(4-(N-methylsulfamoyl)phenyl)isoxazolo[5,4-b]pyridine-4-carboxamide

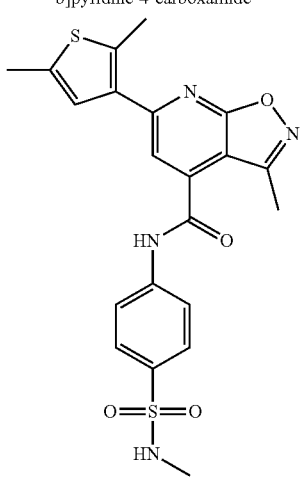

TABLE 2-continued

A1007: (Enamine, Z27683046) 1-phenyl-N-(4-sulfamoylphenyl)-3-(thiophen-2-yl)-1H-pyrazole-4-carboxamide

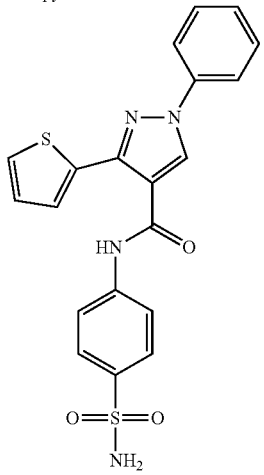

A1008: (ChemDiv, E456-2276) 2-(3-methoxyphenyl)-1-oxo-N-(4-sulfamoylphenyl)-1,2-dihydroisoquinoline-4-carboxamide

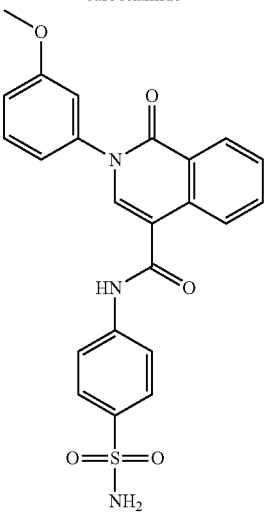 [SMILES: COc1cccc(-n2cc(C(=O)Nc3ccc(S(N)(=O)=O)cc3)c3ccccc3c2=O)c1]

A1009: (Aldrich, 53183721) N-(2-hydroxy-1H-benzo[d]imidazol-6-yl)-2-(pyridin-3-yl)quinoline-4-carboxamide

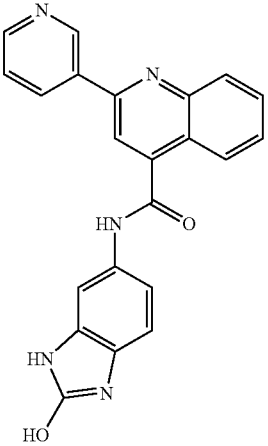 [SMILES: O=C(Nc1ccc2nc(O)[nH]c2c1)c1cc(-c2cccnc2)nc2ccccc12]

Notably, several of the so identified compounds showed significant in vitro antiviral activity as shown below, while additional compounds were identified in iterative computational screens based on A0259 and the activity of tested compounds from earlier screens. Table 3 below depicts results from the above iterative screens.
TABLE 3
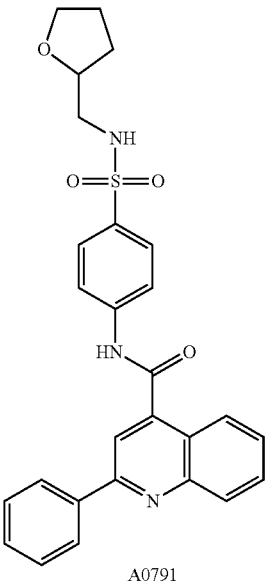 [SMILES: O=C(Nc1ccc(S(=O)(=O)NCC2CCCO2)cc1)c1cc(-c2ccccc2)nc2ccccc12 ; "A0791"]
A0791
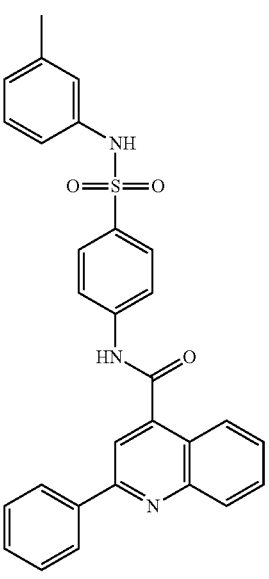
A0792
TABLE 3-continued
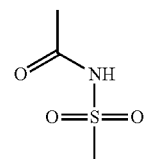
A0795
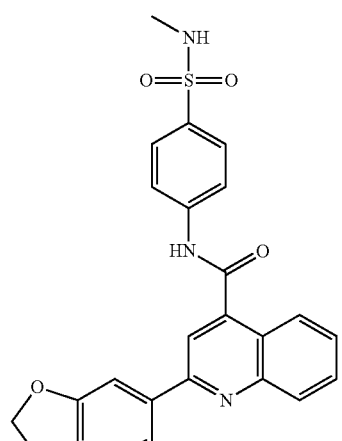
A0801
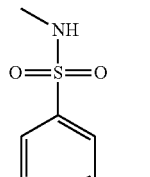
A0802

TABLE 3-continued
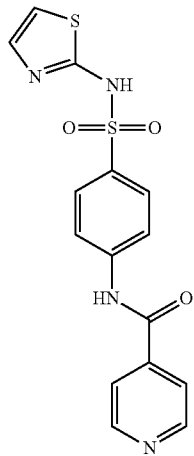
A0804
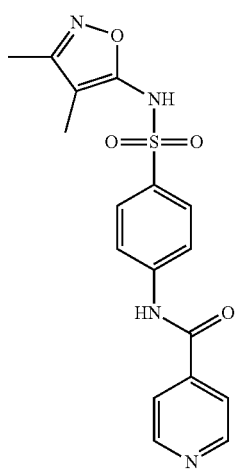
A0805
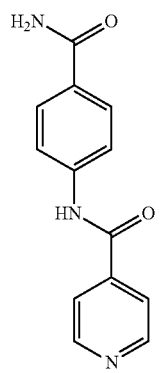
A0806
TABLE 3-continued
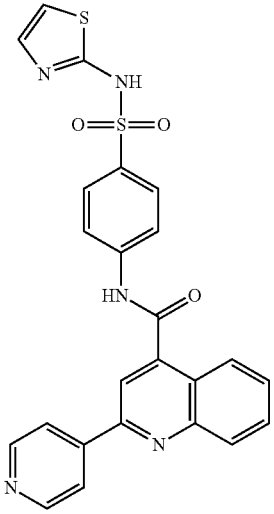
A0843
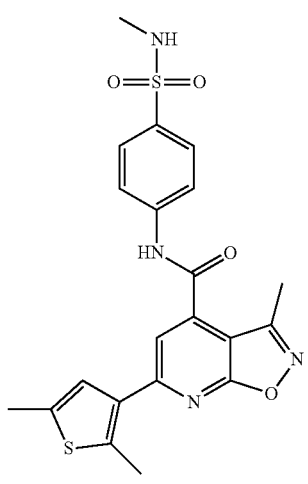
A1006
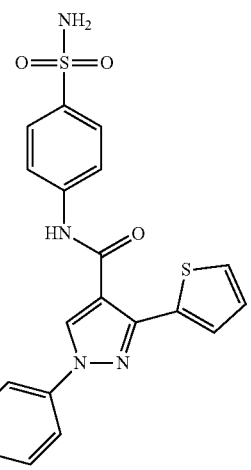
A1007

TABLE 3-continued
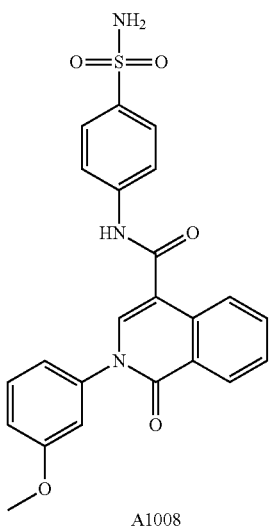 [SMILES: COc1cccc(-n2cc(C(=O)Nc3ccc(S(N)(=O)=O)cc3)c3ccccc3c2=O)c1 ; "A1008"]
A1008
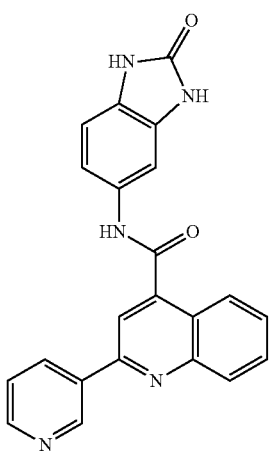
A1009
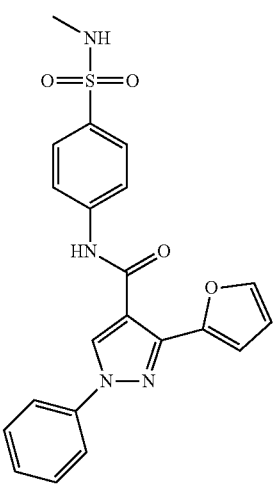
A1010
TABLE 3-continued
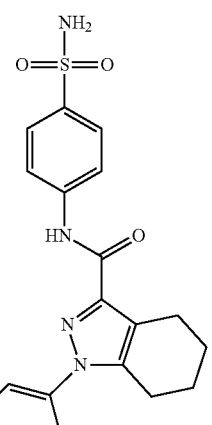
A1011
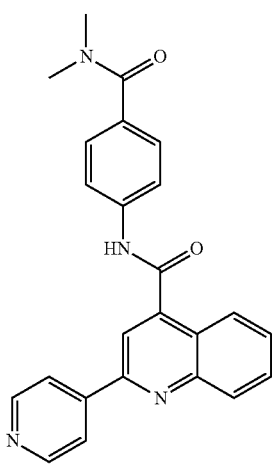
A1012
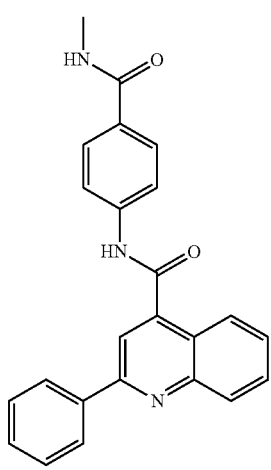
A1013

TABLE 3-continued
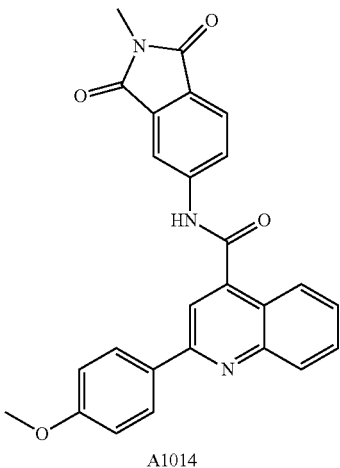
A1014
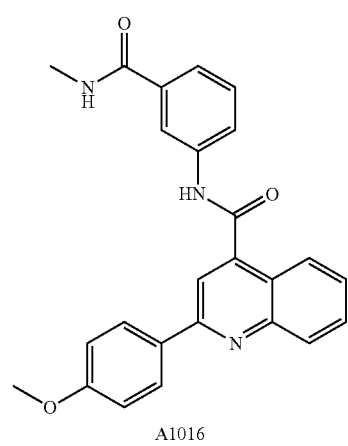
A1016
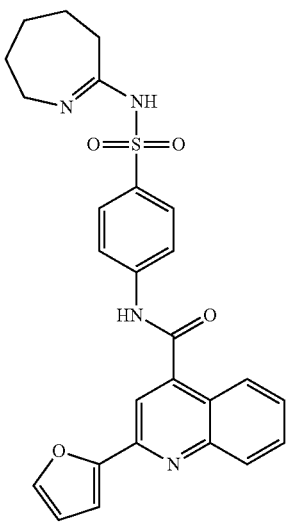
A1017
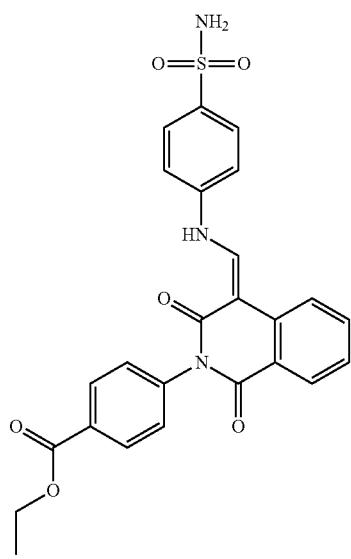
A1018
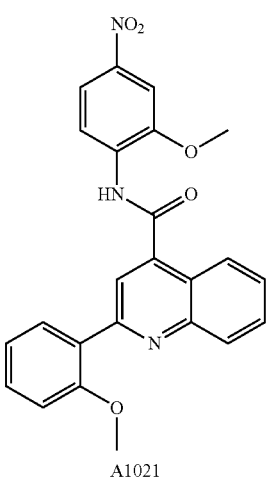
A1021
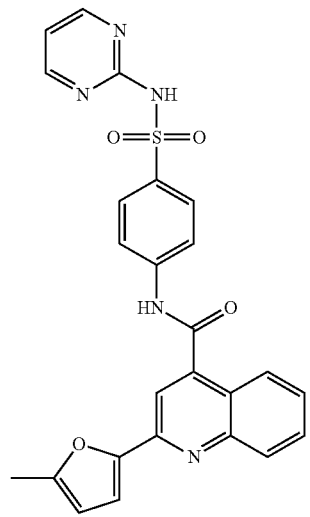
A1022

TABLE 3-continued
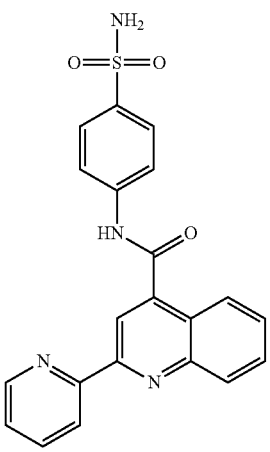
A1025
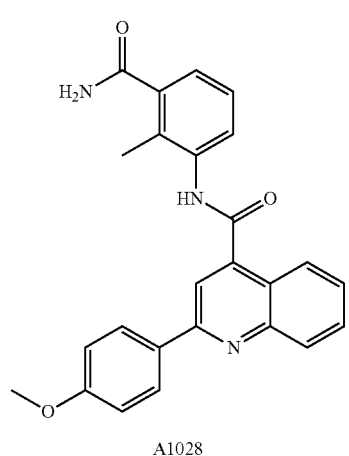
A1028
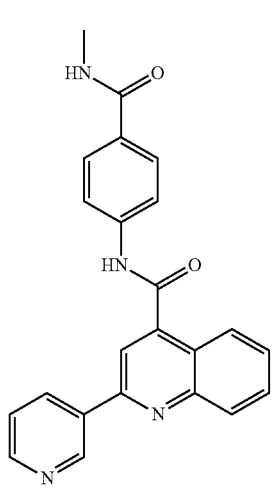
A1030
TABLE 3-continued
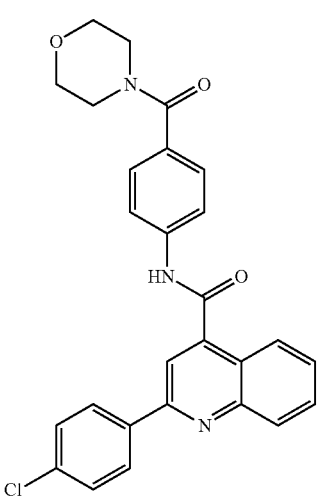
A1031
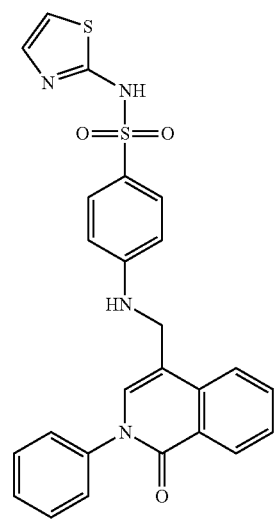
A1032

TABLE 3-continued
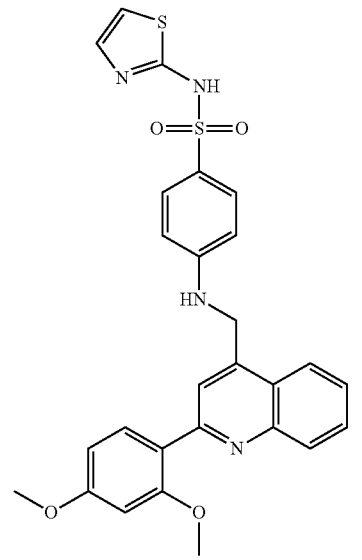
A1033
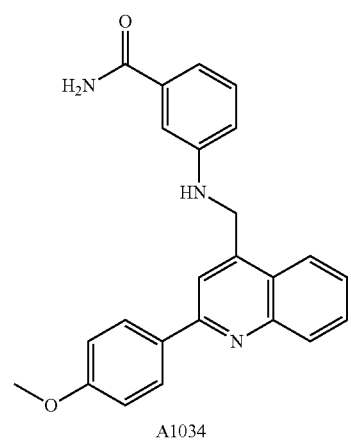
A1034
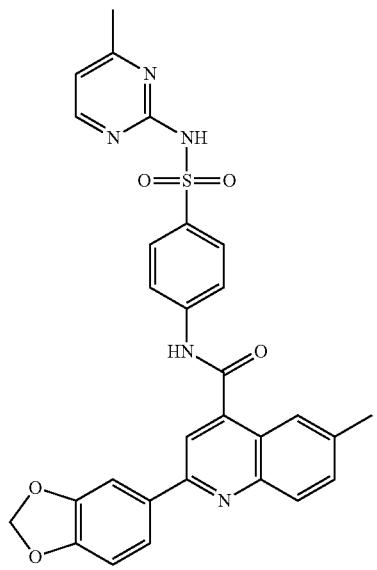
A1090
TABLE 3-continued
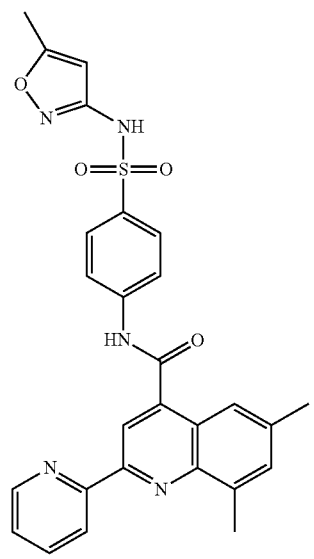
A1093
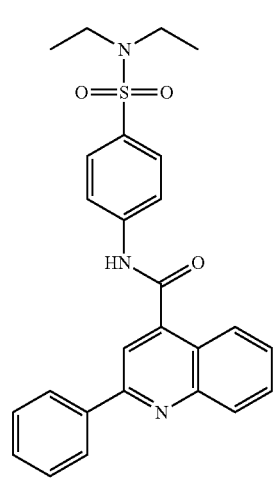
A1097
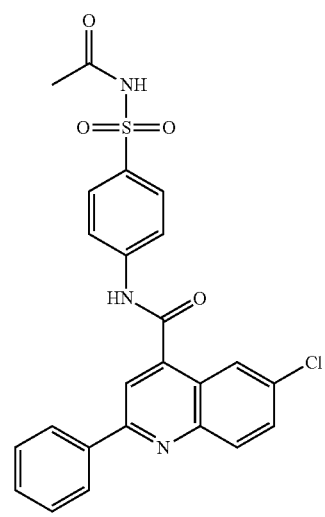
A1098

TABLE 3-continued
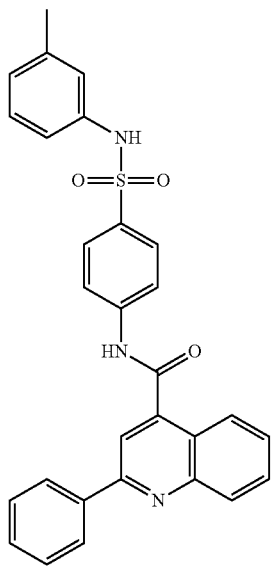
A1100
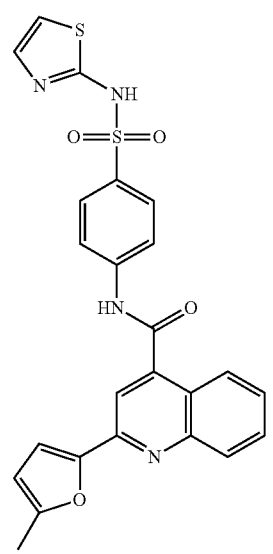
A1101
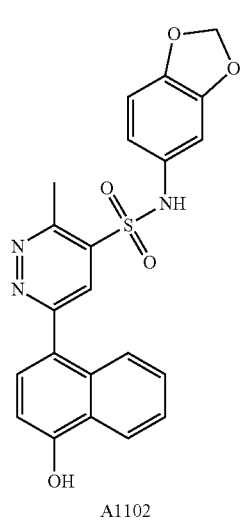
A1102
TABLE 3-continued
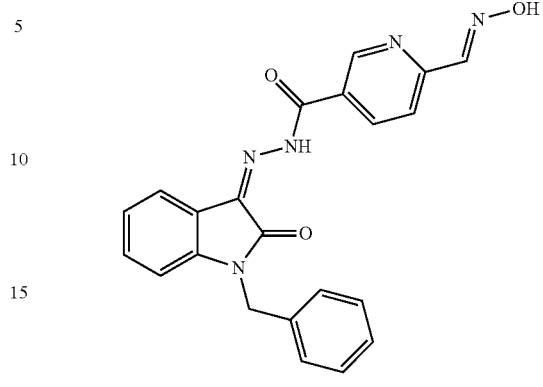
A1103
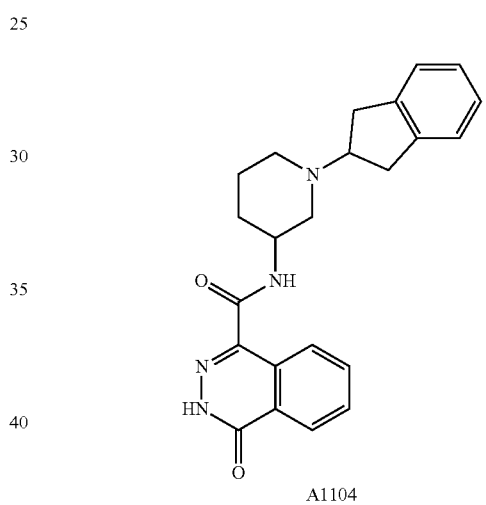
A1104
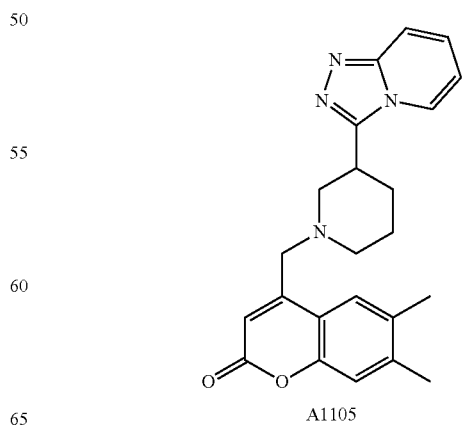
A1105

TABLE 3-continued
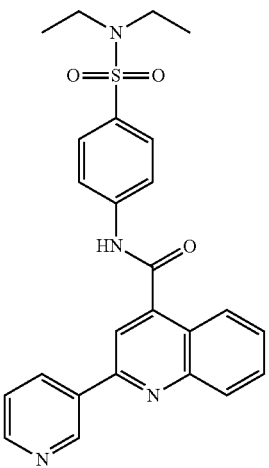
A1107
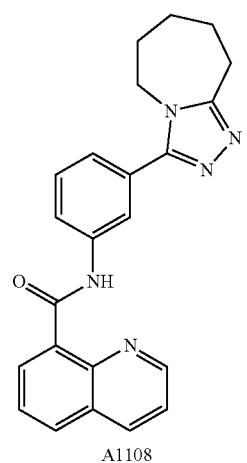
A1108
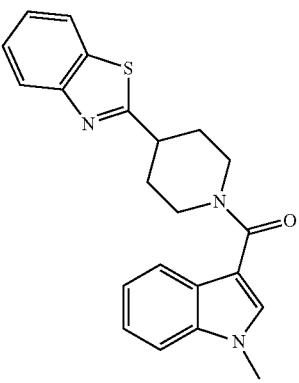
A1109
TABLE 3-continued
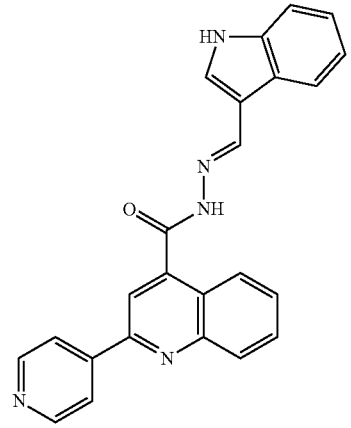
A1110
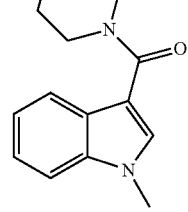
A1112
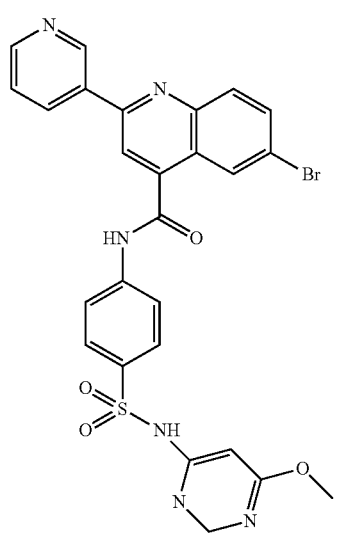
1092

TABLE 3-continued

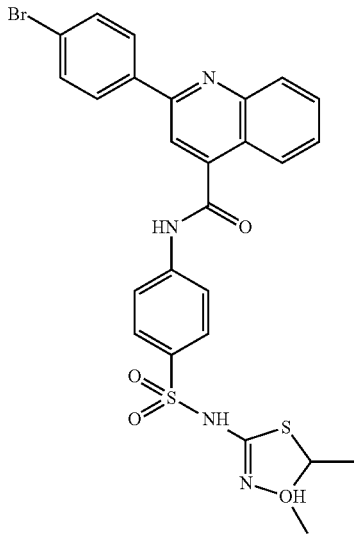

1023

Several of the above compounds (A796, A800, A1005, A1023, A1033, A1092) were further tested in IC50 screens and hemagglutination substantially as described above. As can be readily seen from the results, all compounds exhibited significant antiviral activity and in most cases very moderate toxicity. Most remarkably, these compounds were primarily identified without the need for massive wet-screening of candidate compounds using a particular cell-based system, but were identified using computational analysis. Consequently, it should be appreciated that new antiviral drugs can be indentified in an in silico model that can produce validated pharmacophores, and that the so identified validated pharmacophores can then be used in a secondary computational screen for conformers to provide a defined set of scaffolds that can then be further evaluated in vitro and/or in vivo.

It should be apparent to those skilled in the art that many more modifications besides those already described are possible without departing from the inventive concepts herein. The inventive subject matter, therefore, is not to be restricted except in the spirit of the appended claims. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

The invention claimed is:

1. A pharmaceutical composition comprising N-(4-(N-(quinoxalin-2-yl)sulfamoyl)phenyl)-2-(p-tolyl)quinoline-4-carboxamide;
   wherein the compound is present in the composition in an amount effective to reduce viral propagation of a virus belonging to the family of an orthomyxoviridae when the composition is administered to a person in need thereof.

* * * * *